(12) United States Patent
Wang et al.

(10) Patent No.: US 10,036,008 B2
(45) Date of Patent: Jul. 31, 2018

(54) SCREENING OF NUCLEIC ACID AGENTS VIA PARTICLE DISPLAY

(71) Applicant: The Regents of the University of California, Oakland, CA (US)

(72) Inventors: Jinpeng Wang, Goleta, CA (US); Hyongsok Soh, Santa Barbara, CA (US); Qiang Gong, Goleta, CA (US)

(73) Assignee: The Regents of the University of California, Oakland, CA (US)

( * ) Notice: Subject to any disclaimer, the term of this patent is extended or adjusted under 35 U.S.C. 154(b) by 474 days.

(21) Appl. No.: 14/647,775

(22) PCT Filed: Nov. 21, 2013

(86) PCT No.: PCT/US2013/071318
§ 371 (c)(1),
(2) Date: May 27, 2015

(87) PCT Pub. No.: WO2014/088830
PCT Pub. Date: Jun. 12, 2014

(65) Prior Publication Data
US 2016/0130575 A1   May 12, 2016

Related U.S. Application Data

(60) Provisional application No. 61/733,809, filed on Dec. 5, 2012.

(51) Int. Cl.
C12N 15/10 (2006.01)
C12N 15/115 (2010.01)
(Continued)

(52) U.S. Cl.
CPC ..... *C12N 15/1048* (2013.01); *C12N 15/1037* (2013.01); *C12N 15/115* (2013.01);
(Continued)

(58) Field of Classification Search
None
See application file for complete search history.

(56) References Cited

U.S. PATENT DOCUMENTS

2012/0021940 A1   1/2012   Guthold et al.

FOREIGN PATENT DOCUMENTS

WO   WO 200048000   8/2000
WO   2005003291   1/2005
(Continued)

OTHER PUBLICATIONS

Ahmad, Kareem M. et al; "Probing the Limits of Aptamer Affinity with a Microfluidic SELEX Platform"; *PloS one* vol.6, issue 11; e27051; pp. 1-8; (Nov. 2011).
(Continued)

*Primary Examiner* — Kaijiang Zhang
(74) *Attorney, Agent, or Firm* — Bozicevic, Field & Francis LLP; Michael B. Rubin

(57) ABSTRACT

The present disclosure provides a method for identifying one or more nucleic acid agents, e.g., aptamers, having a desired property from a mixture of candidate nucleic acid agents. The method generally includes immobilizing the mixture of candidate nucleic acid agents onto particles, wherein only a subset of the candidate nucleic acid agents are immobilized on any one of the particles, and wherein the subset is present in multiple copies. The particles are exposed to a target, and particles including candidate nucleic acid agents having the desired property are isolated. In this way, one or more nucleic acid agents having the desired property may be identified. Related compositions and nucleic acid agents identified as having one or more desired properties are also provided.

19 Claims, 10 Drawing Sheets

(51) Int. Cl.
C40B 30/04 (2006.01)
C12Q 1/6811 (2018.01)
(52) U.S. Cl.
CPC .... C12N 2310/16 (2013.01); C12N 2310/351 (2013.01); C12N 2320/11 (2013.01); C12N 2320/13 (2013.01); C12Q 1/6811 (2013.01); C12Q 2541/101 (2013.01); C40B 30/04 (2013.01)

(56) References Cited

FOREIGN PATENT DOCUMENTS

| WO | WO 2012041633 | 4/2012 |
|---|---|---|
| WO | 2012152711 | 11/2012 |

OTHER PUBLICATIONS

Aquino-Jarquin et al; "RNA Aptamer Evolution: Two Decades of SELEction"; Int. J. Mol. Sci. 12; pp. 9155-9171; (2011).
Bock, Louis C., et al; "Selection of single-stranded DNA molecules that bind and inhibit human thrombin"; Nature vol. 355; pp. 564-566; (Feb. 6, 1992).
Boder, Eric T., et al; "Yeast surface display for screening combinatorial polypeptide libraries"; Nature biotechnology, vol. 15; pp. 553-557; (Jun. 1997).
Boder, Eric T., et al; "Optimal screening of surface-displayed polypeptide libraries"; Biotechnology progress, vol. 14, No. 1; pp. 55-62; (1998).
Bunka, David H., et al; "Aptamers come of age—at last"; Nature reviews. Microbiology, vol. 4; pp. 588-596; (Aug. 2006).
Burmeister, Paula. E. et al; "Direct In Vitro Selection of a 2'-O-Methyl Aptamer to VEGF"; Chemistry & Biology, vol. 12; pp. 25-33; (Jan. 2005).
Chao, Ginger, et al; "Isolating and engineering human antibodies using yeast surface display"; Nature protocols vol. 1, No. 2; pp. 755-768; (2006).
Cho, Minseon,. et al; "Quantitative selection of DNA aptamers through microfluidic selection and high-throughput sequencing"; PNAS, vol. 107, No. 35; pp. 15373-15378; (Aug. 31, 2010).
Dhingra, Vikas, et al; "New frontiers in proteomics research: A perspective";.International journal of pharmaceutics 299; pp. 1-18; (2005).
Diehl, Frank, et al; "BEAMing: single-molecule PCR on microparticles in water-in-oil emulsions"; Nature methods, vol. 3, No. 7; pp. 551-559; (Jul. 2006).
Dressman, Devin, et al; "Transforming single DNA molecules into fluorescent magnetic particles for detection and enumeration of genetic variations"; PNAS, vol. 100, No. 15; pp. 8817-8822; (Jul. 22, 2003).
Ellington, Andrew D., et al; "In vitro selection of RNA molecules that bind specific ligands"; Nature, vol. 346; pp. 818-822; (Aug. 30, 1990).
Feldhaus, Michael J. et al; "Flow-cytometric isolation of human antibodies from a nonimmune Saccharomyces cerevisiae surface display library"; Nature biotechnology vol. 21; pp. 163-170; (Feb. 2003).
Francisco, Joseph A.; et al; "Production and Fluorescence-Activated Cell Sorting of Escherichia coli Expressing a Functional Antibody Fragment on the External Surface"; Proceedings of the National Academy of Sciences USA, 90; pp. 10444-10448; (1993).
Gold, Larry, et al. Aptamer-Based Multiplexed Proteomic Technology for Biomarker Discovery; PloS One, vol. 5, Issue 12; e15004; pp. 1-17; (Dec. 2010).
Gold, Larry, et al; "Aptamers and the RNA World, Past and Present"; Cold Spring Harbor Perspectives in Biology 4; pp. 1-11; (2012).
Herzenberg, Leonore A., et al; "Interpreting flow cytometry data: a guide for the perplexed"; Nature immunology, vol. 7, No. 7; pp. 681-685; (Jul. 2006).
Irvine, Doug, et al; "SELEXION. Systematic evolution of ligands by exponential enrichment with integrated optimization by non-linear analysis"; Journal of molecular Biology, 222; pp. 739-761; (1991).
Jellinek, Derek, et al; "Potent 2'-Amino-2'-deoxypyrimidine RNA Inhibitors of Basic Fibroblast Growth Factor"; Biochemistry 34; pp. 11363-11372; (1995).
Kang, Jonghoon, et al; "The enhancement of PCR amplification of a random sequence DNA library by DMSO and betaine: application to in vitro combinatorial selection of aptamers"; Journal of biochemical and biophysical methods 64; pp. 147-151; (2005).
Keefe, Anthony D., et al; "Aptamers as therapeutics"; Nature reviews. Drug discovery vol. 9; pp. 537-550; (Jul. 2010).
Porreca, Gregory. J.; et al; "Polony DNA sequencing"; Current Protocols in Molecular Biology / Chapter 7, Unit 7.8; 22 pages; (2006).
Plaxco, Kevin W., et al; "Switch-based biosensors: a new approach towards real-time, in vivo molecular detection"; Trends in biotechnology vol. 29, No. 1; pp. 1-5; (Jan. 2011).
Qian, Jiangrong., et al; "Generation of highly specific aptamers via micromagnetic selection"; Analytical chemistry 81; pp. 5490-5495; (2009).
Ruckman, J. et al; "2'-Fluoropyrimidine RNA-based aptamers to the 165-amino acid form of vascular endothelial growth factor (VEGF165). Inhibition of receptor binding and VEGF-induced vascular permeability through interactions requiring the exon 7-encoded domain"; The Journal of biological chemistry 273; pp. 20556-20567; (1998).
Shao, Keke, et al; "Emulsion PCR: A High Efficient Way of PCR Amplification of Random DNA Libraries in Aptamer Selection"; PLoS ONE 6(9); pp. e24910 (Sep. 2011).
Stoltenburg, R., et al; "SELEX—a (r)evolutionary method to generate high-affinity nucleic acid ligands"; Biomolecular engineering 24; pp. 381-403; (2007).
Tasset, D. M., et al; "Oligonucleotide inhibitors of human thrombin that bind distinct epitopes"; Journal of molecular biology 272; pp. 688-698; (1997).
Tuerk, C. & Gold, L.; "Systematic evolution of ligands by exponential enrichment: RNA ligands to bacteriophage T4 DNA polymerase"; Science 249, pp. 505-510; (1990).
Vaught, J. D. et al; "Expanding the chemistry of DNA for in vitro selection"; Journal of the American Chemical Society 132; pp. 4141-4151; (2010).
Vant-Hull, B., et al; "Theoretical principles of in vitro selection using combinatorial nucleic acid libraries"; Current protocols in nucleic acid chemistry / edited by Serge L. Beaucage . . . [et al.] Chapter 9, Unit 9; 1 page; (2000).
Wang, J.,et al; "Influence of Target Concentration and Background Binding on In Vitro Selection of Affinity Reagents"; PLoS ONE 7; pp. e43940; (2012).
Willis, M. C. et al; "Liposome-anchored vascular endothelial growth factor aptamers"; Bioconjugate chemistry 9; pp. 573-582; (1998).
Zuker, M.; "Mfold web server for nucleic acid folding and hybridization prediction"; Nucleic acids research 31; pp. 3406-3415; (2003).
Wang Jinpeng et al; (2014) "Particle display: a quantitative screening method for generating high-affinity aptamers"; Angew Chem Int Ed Engl. 53(19); pp. 4796-4801.
Yang Xianbi N et al; (2003) "Immunofluorescence assay and flow-cytometry selection of bead-bound aptamers"; Nucleic Acids Res. 31(10):e54 pp. 1-8.

Figure 9A

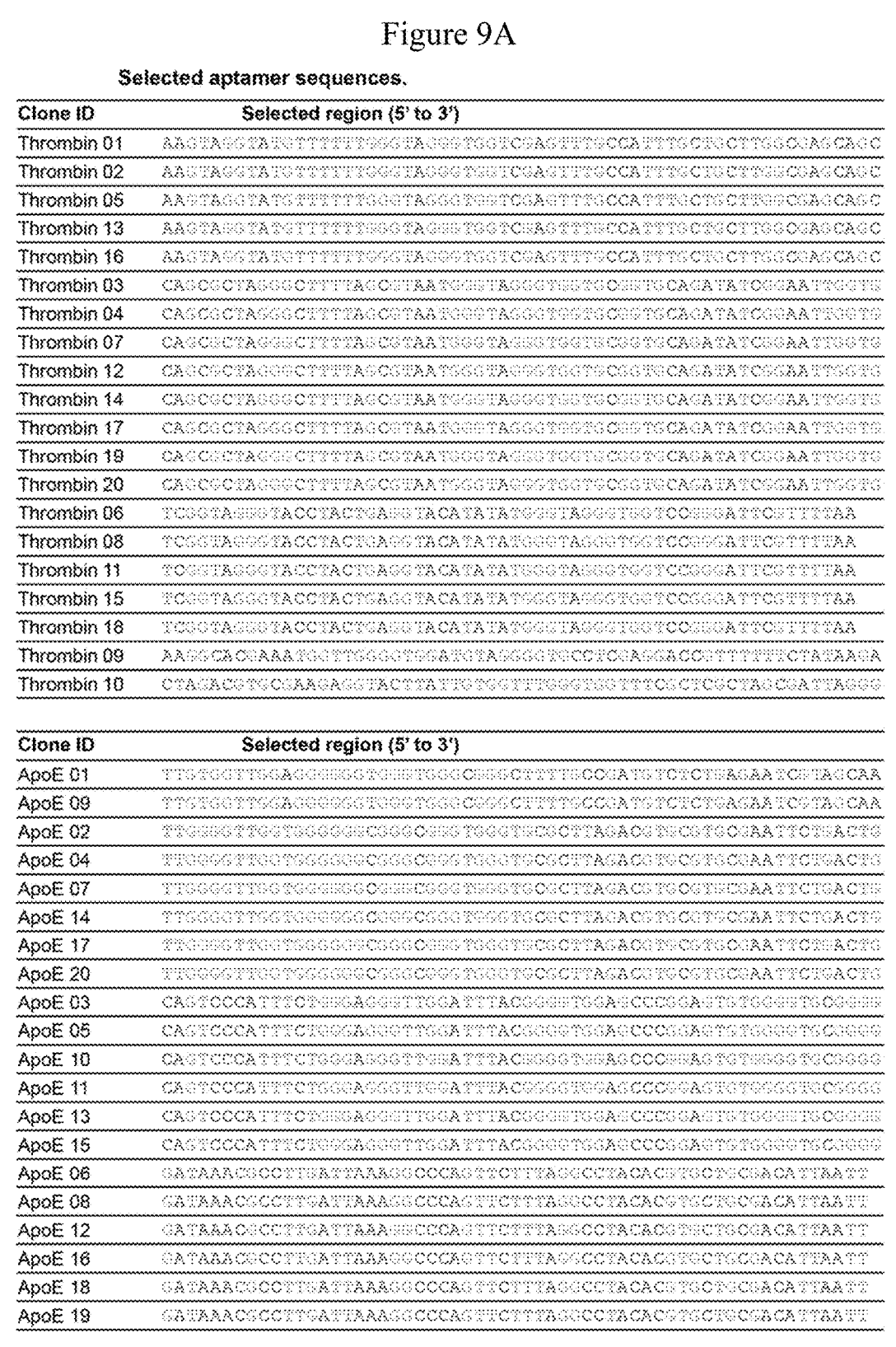

Selected aptamer sequences.

| Clone ID | Selected region (5' to 3') |
|---|---|
| Thrombin 01 | |
| Thrombin 02 | |
| Thrombin 05 | |
| Thrombin 13 | |
| Thrombin 16 | |
| Thrombin 03 | |
| Thrombin 04 | |
| Thrombin 07 | |
| Thrombin 12 | |
| Thrombin 14 | |
| Thrombin 17 | |
| Thrombin 19 | |
| Thrombin 20 | |
| Thrombin 06 | |
| Thrombin 08 | |
| Thrombin 11 | |
| Thrombin 15 | |
| Thrombin 18 | |
| Thrombin 09 | |
| Thrombin 10 | |

| Clone ID | Selected region (5' to 3') |
|---|---|
| ApoE 01 | |
| ApoE 09 | |
| ApoE 02 | |
| ApoE 04 | |
| ApoE 07 | |
| ApoE 14 | |
| ApoE 17 | |
| ApoE 20 | |
| ApoE 03 | |
| ApoE 05 | |
| ApoE 10 | |
| ApoE 11 | |
| ApoE 13 | |
| ApoE 15 | |
| ApoE 06 | |
| ApoE 08 | |
| ApoE 12 | |
| ApoE 16 | |
| ApoE 18 | |
| ApoE 19 | |

Figure 9B

Selected aptamer sequences (continued).

| Clone ID | Selected region (5' to 3') |
|---|---|
| PAI-1 01 | CATTGAGATAGCTAGTTGTAGCTGCGTCATAGGCTGGGTTGGGTCTAGGGTTGGGGTG |
| PAI-1 02 | CATTGAGATAGCTAGTTGTAGCTGCGTCATAGGCTGGGTTGGGTCTAGGGTTGGGGTG |
| PAI-1 07 | CATTGAGATAGCTAGTTGTAGCTGCGTCATAGGCTGGGTTGGGTCTAGGGTTGGGGTG |
| PAI-1 10 | CATTGAGATAGCTAGTTGTAGCTGCGTCATAGGCTGGGTTGGGTCTAGGGTTGGGGTG |
| PAI-1 11 | CATTGAGATAGCTAGTTGTAGCTGCGTCATAGGCTGGGTTGGGTCTAGGGTTGGGGTG |
| PAI-1 12 | CATTGAGATAGCTAGTTGTAGCTGCGTCATAGGCTGGGTTGGGTCTAGGGTTGGGGTG |
| PAI-1 14 | CATTGAGATAGCTAGTTGTAGCTGCGTCATAGGCTGGGTTGGGTCTAGGGTTGGGGTG |
| PAI-1 17 | CATTGAGATAGCTAGTTGTAGCTGCGTCATAGGCTGGGTTGGGTCTAGGGTTGGGGTG |
| PAI-1 18 | CATTGAGATAGCTAGTTGTAGCTGCGTCATAGGCTGGGTTGGGTCTAGGGTTGGGGTG |
| PAI-1 19 | CATTGAGATAGCTAGTTGTAGCTGCGTCATAGGCTGGGTTGGGTCTAGGGTTGGGGTG |
| PAI-1 04 | CGGGACACGGGTGACAAGTGGTTGTGTGGATGGAGGGCATGTCACCCCTGG |
| PAI-1 05 | CGGGACACGGGTGACAAGTGGTTGTGTGGATGGAGGGCATGTCACCCCTGG |
| PAI-1 08 | CGGGACACGGGTGACAAGTGGTTGTGTGGATGGAGGGCATGTCACCCCTGG |
| PAI-1 09 | CGGGACACGGGTGACAAGTGGTTGTGTGGATGGAGGGCATGTCACCCCTGG |
| PAI-1 13 | CGGGACACGGGTGACAAGTGGTTGTGTGGATGGAGGGCATGTCACCCCTGG |
| PAI-1 15 | CGGGACACGGGTGACAAGTGGTTGTGTGGATGGAGGGCATGTCACCCCTGG |
| PAI-1 16 | CGGGACACGGGTGACAAGTGGTTGTGTGGATGGAGGGCATGTCACCCCTGG |
| PAI-1 03 | CACTTCGATGTCGTGAGTGGGGTGTGGTGGGGTGACCTTGCATCGGCCC |
| PAI-1 20 | CACTTCGATGTCGTGAGTGGGGTGTGGTGGGGTGACCTTGCATCGGCCC |
| PAI-1 06 | GACAGGTGTGTGTGGGGCGAGGGTTGGGTCCCGGGCCTTAGAAGGCGC |

| Clone ID | Selected region (5' to 3') |
|---|---|
| 4-1BB 01 | ATCCACGAAGTAGACTGTCTAGGTTGGGTAGGGTGGTGACAGTGTCTGGGAAGGCTGCGC |
| 4-1BB 02 | ATCCACGAAGTAGACTGTCTAGGTTGGGTAGGGTGGTGACAGTGTCTGGGAAGGCTGCGC |
| 4-1BB 06 | ATCCACGAAGTAGACTGTCTAGGTTGGGTAGGGTGGTGACAGTGTCTGGGAAGGCTGCGC |
| 4-1BB 10 | ATCCACGAAGTAGACTGTCTAGGTTGGGTAGGGTGGTGACAGTGTCTGGGAAGGCTGCGC |
| 4-1BB 12 | ATCCACGAAGTAGACTGTCTAGGTTGGGTAGGGTGGTGACAGTGTCTGGGAAGGCTGCGC |
| 4-1BB 14 | ATCCACGAAGTAGACTGTCTAGGTTGGGTAGGGTGGTGACAGTGTCTGGGAAGGCTGCGC |
| 4-1BB 15 | ATCCACGAAGTAGACTGTCTAGGTTGGGTAGGGTGGTGACAGTGTCTGGGAAGGCTGCGC |
| 4-1BB 07 | GTCAGATTCCACTATAGTAGGTTGGGTAGGGTGGTCCAGTGGATGATATGTCGTAGGGG |
| 4-1BB 08 | GTCAGATTCCACTATAGTAGGTTGGGTAGGGTGGTCCAGTGGATGATATGTCGTAGGGG |
| 4-1BB 09 | GTCAGATTCCACTATAGTAGGTTGGGTAGGGTGGTCCAGTGGATGATATGTCGTAGGGG |
| 4-1BB 11 | GTCAGATTCCACTATAGTAGGTTGGGTAGGGTGGTCCAGTGGATGATATGTCGTAGGGG |
| 4-1BB 17 | GTCAGATTCCACTATAGTAGGTTGGGTAGGGTGGTCCAGTGGATGATATGTCGTAGGGG |
| 4-1BB 18 | GTCAGATTCCACTATAGTAGGTTGGGTAGGGTGGTCCAGTGGATGATATGTCGTAGGGG |
| 4-1BB 19 | GTCAGATTCCACTATAGTAGGTTGGGTAGGGTGGTCCAGTGGATGATATGTCGTAGGGG |
| 4-1BB 20 | GTCAGATTCCACTATAGTAGGTTGGGTAGGGTGGTCCAGTGGATGATATGTCGTAGGGG |
| 4-1BB 04 | GTCAGATTCCACTATAGTAGGTTGGGTAGGGTGGTCCAGTGGATGATATGTCGTAGGGG |
| 4-1BB 16 | GTCAGATTCCACTATAGTAGGTTGGGTAGGGTGGTCCAGTGGATGATATGTCGTAGGGG |
| 4-1BB 03 | GCGGGTGTAAGTGTTGTTGGGCGGGGCGGGGTTGGAGAGGACGAGGGC |
| 4-1BB 13 | GCGGGTGTAAGTGTTGTTGGGCGGGGCGGGGTTGGAGAGGACGAGGGC |
| 4-1BB 05 | ATGCGAGTAGGTTGTAGGGGTGGTCGTTGGATATCATTTATAGCCCTGCGAGTCGC |

SEQUENCE LISTING

<160> NUMBER OF SEQ ID NOS: 19

<210> SEQ ID NO 1
<211> LENGTH: 60
<212> TYPE: DNA
<213> ORGANISM: Artificial Sequence
<220> FEATURE:
<223> OTHER INFORMATION: Synthetic DNA Aptamer Sequence

<400> SEQUENCE: 1
aagtaggtat gtttttggg tagggtggtc gagtttgcca tttgctgctt ggcgagcagc    60

<210> SEQ ID NO 2
<211> LENGTH: 60
<212> TYPE: DNA
<213> ORGANISM: Artificial Sequence
<220> FEATURE:
<223> OTHER INFORMATION: Synthetic DNA Aptamer Sequence

<400> SEQUENCE: 2
cagcgctagg gcttttagcg taatgggtag ggtggtgcgg tgcagatatc ggaattggtg    60

<210> SEQ ID NO 3
<211> LENGTH: 58
<212> TYPE: DNA
<213> ORGANISM: Artificial Sequence
<220> FEATURE:
<223> OTHER INFORMATION: Synthetic DNA Aptamer Sequence

<400> SEQUENCE: 3
tcggtagggt acctactgag gtacatatat gggtagggtg gtccgggatt cgttttaa    58

<210> SEQ ID NO 4
<211> LENGTH: 60
<212> TYPE: DNA
<213> ORGANISM: Artificial Sequence
<220> FEATURE:
<223> OTHER INFORMATION: Synthetic DNA Aptamer Sequence

<400> SEQUENCE: 4
aaggcacgaa atggttgggg tggatgtagg ggtgcctcga ggaccgtttt ttctataaga    60

<210> SEQ ID NO 5
<211> LENGTH: 60
<212> TYPE: DNA
<213> ORGANISM: Artificial Sequence
<220> FEATURE:
<223> OTHER INFORMATION: Synthetic DNA Aptamer Sequence

<400> SEQUENCE: 5
ctagacgtgc gaagaggtac ttattgtggt ttgggtggtt tcgctcgcta gcgattaggg    60

<210> SEQ ID NO 6
<211> LENGTH: 60
<212> TYPE: DNA
<213> ORGANISM: Artificial Sequence
<220> FEATURE:
<223> OTHER INFORMATION: Synthetic DNA Aptamer Sequence

<400> SEQUENCE: 6
ttgtggttgg aggggggtgg gtgggcgggc ttttgccgat gtctctgaga atcgtagcaa    60

<210> SEQ ID NO 7
<211> LENGTH: 60
<212> TYPE: DNA
<213> ORGANISM: Artificial Sequence
<220> FEATURE:
<223> OTHER INFORMATION: Synthetic DNA Aptamer Sequence

<400> SEQUENCE: 7
ttggggttgg tgggggcgg gcgggtgggt gcgcttagac gtgcgtgcga attctgactg    60

<210> SEQ ID NO 8
<211> LENGTH: 60
<212> TYPE: DNA
<213> ORGANISM: Artificial Sequence
<220> FEATURE:
<223> OTHER INFORMATION: Synthetic DNA Aptamer Sequence

<400> SEQUENCE: 8
cagtcccatt tctgggaggg ttggatttac ggggtggagc ccggagtgtg gggtgcgggg    60

<210> SEQ ID NO 9
<211> LENGTH: 59
<212> TYPE: DNA
<213> ORGANISM: Artificial Sequence
<220> FEATURE:
<223> OTHER INFORMATION: Synthetic DNA Aptamer Sequence

<400> SEQUENCE: 9
gataaacgcc ttgattaaag gcccagttct ttaggcctac acgtgctgcg acattaatt    59

<210> SEQ ID NO 10
<211> LENGTH: 60
<212> TYPE: DNA
<213> ORGANISM: Artificial Sequence

```
<220> FEATURE:
<223> OTHER INFORMATION: Synthetic DNA Aptamer Sequence

<400> SEQUENCE: 10
cattgagata gctagttgta gctgcgtcat aggctgggtt gggtctagtg gttgggtgtg      60

<210> SEQ ID NO 11
<211> LENGTH: 60
<212> TYPE: DNA
<213> ORGANISM: Artificial Sequence
<220> FEATURE:
<223> OTHER INFORMATION: Synthetic DNA Aptamer Sequence

<400> SEQUENCE: 11
cacttcgatt gtcgtggagg tgggggtggg tgtgggtggg gtgagaccgt gcatcggccg      60

<210> SEQ ID NO 12
<211> LENGTH: 60
<212> TYPE: DNA
<213> ORGANISM: Artificial Sequence
<220> FEATURE:
<223> OTHER INFORMATION: Synthetic DNA Aptamer Sequence

<400> SEQUENCE: 12
cggggacacg gggtggacga agtgggttgt gtgtggatgg gaggggcatg tcacccctgg      60

<210> SEQ ID NO 13
<211> LENGTH: 60
<212> TYPE: DNA
<213> ORGANISM: Artificial Sequence
<220> FEATURE:
<223> OTHER INFORMATION: Synthetic DNA Aptamer Sequence

<400> SEQUENCE: 13
gacatggtgg gtgtgtgggg gtgggcggag ggttggtggt ccgctggcct tagaaggcgc      60

<210> SEQ ID NO 14
<211> LENGTH: 60
<212> TYPE: DNA
<213> ORGANISM: Artificial Sequence
<220> FEATURE:
<223> OTHER INFORMATION: Synthetic DNA Aptamer Sequence

<400> SEQUENCE: 14
atccacgaag tagactgtct aggttgggta gggtggtgac agtgtctggg aaggctgcgc      60

<210> SEQ ID NO 15
<211> LENGTH: 60
<212> TYPE: DNA
<213> ORGANISM: Artificial Sequence
<220> FEATURE:
<223> OTHER INFORMATION: Synthetic DNA Aptamer Sequence

<400> SEQUENCE: 15
ggcggtcgta atgtggttgt ggttggtggg gggcgggtgg gttgggagag gacgaggcgc      60

<210> SEQ ID NO 16
<211> LENGTH: 60
<212> TYPE: DNA
<213> ORGANISM: Artificial Sequence
<220> FEATURE:
<223> OTHER INFORMATION: Synthetic DNA Aptamer Sequence

<400> SEQUENCE: 16
gtcagattcc actatagtag gttgggtatg gtggtcgcag tggatgatat gtcgtagggg      60
```

```
<210> SEQ ID NO 17
<211> LENGTH: 59
<212> TYPE: DNA
<213> ORGANISM: Artificial Sequence
<220> FEATURE:
<223> OTHER INFORMATION: Synthetic DNA Aptamer Sequence

<400> SEQUENCE: 17
atgtcgagta ggttgggtag ggtggtcgtt gatatcattt atattccctg ctagtctgc      59

<210> SEQ ID NO 18
<211> LENGTH: 60
<212> TYPE: DNA
<213> ORGANISM: Artificial Sequence
<220> FEATURE:
<223> OTHER INFORMATION: Synthetic DNA Aptamer Sequence

<400> SEQUENCE: 18
gtcagattcc actatagtag gttgggtagg gtggtcgcag tggatgatat gtcgtagggg     60

<210> SEQ ID NO 19
<211> LENGTH: 20
<212> TYPE: DNA
<213> ORGANISM: Artificial Sequence
<220> FEATURE:
<223> OTHER INFORMATION: Forward primer

<400> SEQUENCE: 19
agcagcacag aggtcagatg                                                 20
```

SCREENING OF NUCLEIC ACID AGENTS VIA PARTICLE DISPLAY

CROSS-REFERENCE

This application is a National Stage of International Application No. PCT/US2013/071318, filed Nov. 21, 2013, which application claims the benefit of U.S. Provisional Application No. 61/733,809, filed Dec. 5, 2012, which applications are incorporated herein by reference in their entirety.

STATEMENT REGARDING FEDERALLY SPONSORED RESEARCH

The invention was made with Government support under Grant No. U54 DK093467 and Grant No. R01 AI076899 awarded by the National Institutes of Health (NIH) and Grant No. W911NF-09-D-0001 awarded by the Institute for Collaborative Biotechnologies (ICB) an affiliate of the Department of Defense (DOD). The government has certain rights in the invention.

INTRODUCTION

Since their initial description, aptamers have shown considerable promise as a synthetic alternative to monoclonal antibodies. They possess numerous important advantages, including thermostability, ease of chemical synthesis and modification, and the capacity for reversible folding, all of which are valuable characteristics for diverse applications in molecular diagnostics and therapeutics. Unfortunately, the standard aptamer generation process (i.e., Systematic Evolution of Ligands by Exponential Enrichment (SELEX)) often fails to yield aptamers with comparable affinity and specificity relative to antibodies. See, e.g., Stoltenburg et al. (2007) *Biomolecular Engineering*, 24:381-403. Furthermore, it has been postulated that aptamers based entirely on natural nucleotides without chemical modifications only offer a limited repertoire of chemical interactions and are capable of targeting only ~30% of the human proteome. See, e.g., Vaught et al. (2010) *Journal of the American Chemical Society*, 132:4141-51. These challenges have hindered widespread adoption of aptamers, and there is a critical need for methods that can consistently generate aptamers with superior affinity and specificity against a wider range of targets.

SUMMARY

The present disclosure provides a method for identifying one or more nucleic acid agents, e.g., aptamers, having a desired property from a mixture of candidate nucleic acid agents. The method generally includes immobilizing the mixture of candidate nucleic acid agents onto particles, wherein only a subset of the candidate nucleic acid agents are immobilized on any one of the particles, and wherein the subset is present in multiple copies. The particles are exposed to a target, and particles including candidate nucleic acid agents having the desired property are isolated. In this way, one or more nucleic acid agents having the desired property may be identified. Related compositions and nucleic acid agents identified as having one or more desired properties are also provided.

The present disclosure also provides a quantitative, particle based method of generating and screening candidate aptamers that is fundamentally different than conventional SELEX-based strategies. Generally, a library of aptamer particles (APs) is prepared, wherein each AP displays multiple copies of a unique candidate aptamer sequence on its surface. The APs are exposed to a target and each AP is sorted based on a quantitative analysis of an interaction between the candidate aptamer sequences on the AP and the target. Following sorting, an enriched pool of aptamer particles may be provided which has reduced sequence diversity relative to the original library. One or more rounds of screening may be performed to identify aptamers having desired target interactions. Related compositions and aptamers having one or more desired target interactions are also provided.

The disclosed aptamer screening method offers an important advantage over conventional SELEX-based methods. Using conventional selection methods, it is challenging to discard aptamer sequences that proliferate due to factors such as library synthesis bias (Cho, M. et al. (2010) *Proceedings of the National Academy of Sciences of the United States of America* 107: 15373-8), non-specific background binding (Wang et al. (2012) *PLoS ONE* 7, e43940) and PCR bias (Kang et al. (2005) *Journal of biochemical and biophysical methods* 64:147-51). These effects often lead to the isolation of inferior aptamers or failed selection (Gold et al. (2010) *PloS one* 5, e15004). In contrast, the methods disclosed herein may eliminate the confounding effects of such biases, e.g., by quantitatively measuring an interaction between each individual candidate aptamer sequence and its target at every round, such that aptamers which do not meet selected interaction conditions are effectively discarded regardless of their copy number.

Certain non-limiting aspects of the disclosure are provided below:

1. A method for identifying one or more nucleic acid agents having a desired property from a mixture of candidate nucleic acid agents, wherein the mixture of candidate nucleic acid agents includes a plurality of single stranded nucleic acids, the method including:
    immobilizing the mixture of candidate nucleic acid agents onto a plurality of particles, wherein only a subset of the candidate nucleic acid agents are immobilized on any one of the plurality of particles, and wherein the subset is present in multiple copies;
    exposing the plurality of particles to a target,
    isolating a particle or particles from the plurality of particles, wherein the isolated particle or particles include one or more candidate nucleic acid agents having the desired property; and
    identifying one or more nucleic acid agents having the desired property from the isolated particles.
2. The screening method of 1, wherein the target is a protein target.
3. The screening method of 1, wherein the target is a small molecule target.
4. The screening method of 1, wherein the small molecule target is a toxin.
5. The screening method of 1, wherein the target is a whole cell, a cellular component or a liposome.
6. The screening method of 1 or 2, wherein the single stranded nucleic acids are selected from DNA, RNA, chemically modified DNA, and chemically modified RNA.
7. The screening method of 6, wherein the single stranded nucleic acids are DNA.
8. The screening method of 1 or 2, wherein the single stranded nucleic acids include non-natural nucleic acids.

9. The screening method of any one of 1-8, wherein one or more of the single stranded nucleic acids includes a molecule conjugated thereto.

10. The screening method of 9, wherein the molecule conjugated to one or more of the single stranded nucleic acids is a small molecule.

11. The screening method of 9, wherein the molecule conjugated to one or more of the single stranded nucleic acids is a fluorophore.

12. The screening method of 9, wherein the molecule conjugated to one or more of the single stranded nucleic acids is a peptide.

13. The screening method of 9, wherein the molecule conjugated to one or more of the single stranded nucleic acids is an siRNA.

14. The screening method of any one of 1-13, wherein the desired property is a target binding activity or a target-binding induced activity.

15. The screening method of 14, wherein the target binding activity is affinity, specificity or bi-specificity.

16. The screening method of 15, wherein the target binding activity is specificity, the screening method includes exposing the plurality of particles to a first target and a second target, and wherein the nucleic acid agents having the desired property exhibit a specific binding affinity for either the first target or the second target but not both.

17. The screening method of 16, wherein the first target is a first homolog or splicing variant of a protein and the second target is a second homolog or splicing variant of the protein.

18. The screening method of 16, wherein the first target is a first post-translational modification form of a protein and the second target is a second post-translation modification form of the protein.

19. The screening method of 16, wherein the first target is a protein which has been subjected to a post-translational modification and the second target is a form of the protein which has not been subjected to a post-translational modification.

20. The screening method of 16, wherein the first target is a first conformational form of a protein and the second target is a second conformational form of the protein.

21. The screening method of 15, wherein the target binding activity is bi-specificity, the screening method includes exposing the plurality of particles a first target and a second target, and wherein the nucleic acid agents having the desired property exhibit a specific binding affinity for both the first and second target.

22. The screening method of 21, wherein the first target is a first homolog or splicing variant of a protein and the second target is a second homolog or splicing variant of the protein.

23. The screening method of 21, wherein the first target is a first post-translational modification form of a protein and the second target is a second post-translation modification form of the protein.

24. The screening method of 21, wherein the first target is a protein which has been subjected to a post-translational modification and the second target is a form of the protein which has not been subjected to a post-translational modification.

25. The screening method of 21, wherein the first target is a first conformational form of a protein and the second target is a second conformational form of the protein.

26. The screening method of 15, wherein the target binding activity is specificity, the screening method includes exposing the plurality of particles to a first target labeled with a first detectable label and a second target labeled with a second detectable label, wherein the first detectable label and the second detectable label are different, and wherein the nucleic acid agents having the desired property exhibit a first binding affinity for the first target and a second binding affinity for the second target, wherein the first binding affinity and the second binding affinity are significantly different.

27. The screening method of 15, wherein the target binding activity is bi-specificity, the screening method includes exposing the plurality of particles to a first target labeled with a first detectable label and a second target labeled with a second detectable label, wherein the first detectable label and the second detectable label are different, and wherein the nucleic acid agents having the desired property exhibit a specific binding affinity for both the first and second target.

28. The screening method of 14, wherein the target-binding induced activity is a catalytic activity or a modified catalytic activity.

29. The screening method of 14, wherein the target-binding induced activity is an inhibition activity, an activation activity, or a modification of an inhibition activity or an activation activity.

30. The screening method of 14, wherein the target-binding induced activity is a structure switching activity or a modification of a structure switching activity.

31. The screening method of 14, wherein the target-binding induced activity is a cooperative activity.

32. The screening method of any one of 1-31, wherein the particles are non-magnetic.

33. The screening method of any one of 1-31, wherein the particles are magnetic or paramagnetic.

34. The screening method of any one of 1-33, wherein each particle has at least one dimension of from about 50 nm to about 100 μm.

35. The screening method of 34, wherein the at least one dimension is from about 50 nm to about 1 μm.

36. The screening method of 35, wherein the at least one dimension is from about 50 nm to about 500 nm.

37. The screening method of 36, wherein the at least one dimension is from about 50 nm to about 100 nm.

38. The screening method of 34, wherein the at least one dimension is from about 500 nm to about 100 μm.

39. The screening method of 38, wherein the at least one dimension is from about 1 μm to about 100 μm.

40. The screening method of 39, wherein the at least one dimension is from about 50 μm to about 100 μm.

41. The screening method of any one of 34-40, wherein the at least one dimension is diameter.

42. The screening method of any one of 1-31, wherein the particles include carboxylic acid paramagnetic particles having an average diameter of about 1 μm.

43. The screening method of any one of 1-42, wherein the particles include one or more functional groups positioned on one or more surfaces of the particles.

44. The screening method of 43, wherein the one or more functional groups are selected from amine groups, carboxyl groups, thiol groups, $SiO_2$, EDTA, and boronic acid functional groups.

45. The screening method of any one of 1-42, wherein the particles include one or more members of a specific binding pair on one or more surfaces of the particles.

46. The screening method of 45, wherein the one or more members of a specific binding pair are selected from avidin, streptavidin, Neutravidin®, Captavidin™, and biotin.

47. The screening method of any one of 1-46, wherein the plurality of particles includes from about $1\times10^2$ to about $1\times10^{14}$ particles.

48. The screening method of any one of 1-47, wherein the sequence diversity of the mixture is from about $1\times10^2$ to about $1\times10^{14}$.

49. The screening method of any one of 1-48, wherein each of the particles of the plurality of particles includes from about $1\times10^2$ to about $1\times10^{10}$ candidate nucleic acid agents bound thereto.

50. The screening method of any one of 1-49, wherein the sequence diversity of the subset of the candidate nucleic acid agents immobilized on any one of the plurality of particles is from 1 to $10^6$.

51. The screening method of 50, wherein the sequence diversity of the subset of the candidate nucleic acid agents immobilized on any one of the plurality of particles is from 1 to 100.

52. The screening method of 51, wherein the sequence diversity of the subset of the candidate nucleic acid agents immobilized on any one of the plurality of particles is from 1 to 50.

53. The screening method of 52, wherein the sequence diversity of the subset of the candidate nucleic acid agents immobilized on any one of the plurality of particles is 1.

54. The screening method of any one of 1-53, wherein each of the candidate nucleic acid agents is coupled to a particle of the plurality of particles via a linker.

55. The screening method of 54, wherein the linker is a cleavable linker.

56. The screening method of 54, wherein the linker is a non-cleavable linker.

57. The screening method of 54, wherein the linker is a combination of a cleavable linker and a non-cleavable linker.

58. The screening method of any one of 54-57, wherein the linker is selected from an amino group, biotin, dual-biotin, and thiol group.

59. The screening method of any one of 1-58, wherein the particle or particles that include one or more candidate nucleic acid agents having the desired property are modified as a result of the desired property following exposure to the target, which modification allows the particle or particles that include the one or more candidate nucleic acid agents having the desired property to be isolated.

60. The screening method of 59, wherein the modification includes coupling of a detectable label to the particle or particles.

61. The screening method of 59, wherein the modification includes coupling of two or more different detectable labels to the particle or particles.

62. The screening method of 60, wherein the detectable label is physically detectable, chemically detectable, or optically detectable.

63. The screening method of 62, wherein the detectable label is magnetic or paramagnetic.

64. The screening method of 62, wherein the detectable label is a luminescent label.

65. The screening method of 64, wherein the luminescent label is a fluorescent label.

66. The screening method of 62, wherein the detectable label is a radiolabel.

67. The screening method of any one of 1-66, wherein the isolating step includes sorting the plurality of particles using a technique selected from flow cytometry, fluorescence microscopy, sorting using optical tweezers, sorting using micro-pipettes, and microfluidic magnetic separation.

68. The screening method of 67, wherein the flow cytometry is fluorescence activated cell sorting (FACS) or Ramen flow cytometry.

69. The screening method of any one of 1-68, wherein the isolating step includes contacting the plurality of particles with one or more detectable labels,
    wherein the one or more detectable labels associate to a higher level with particles including one or more candidate nucleic acid agents having the desired property and associate to a lower level with particles which do not include one or more candidate nucleic acid agents having the desired property, or
    wherein the one or more detectable labels associate to a lower level with particles including one or more candidate nucleic acid agents having the desired property and associate to a higher level with particles which do not include one or more candidate nucleic acid agents having the desired property.

70. The screening method of 69, further including quantitating a signal from the detectable labels.

71. The screening method of 70, further including enriching a population of the plurality of particles based on the quantitated signal.

72. The screening method of any one of 1-71, further including introducing one or more mutations into the one or more nucleic acid agents having the desired property.

73. The screening method of any one of 1-72, further including iteratively repeating one or more of the immobilizing, exposing, isolating and identifying steps of 1.

74. The screening method of any one of 69-72, further including iteratively repeating one or more of the contacting step of 69, the quantitating step of 70, the enriching step of 71, and the introducing step of 72.

75. The screening method of any one of 1-74, wherein the method includes preparing the mixture of candidate nucleic acid agents by a method including generating a library of single stranded nucleic acids, wherein each single stranded nucleic acid includes region of randomized sequence.

76. A method for identifying one or more aptamers having a desired property from a mixture of candidate aptamer sequences, the method including:
    immobilizing the mixture of candidate aptamer sequences onto a plurality of particles, wherein only a subset of the candidate aptamer sequences are immobilized on any one of the plurality of particles, and wherein the subset is present in multiple copies;
    exposing the plurality of particles to a target,
    isolating a particle or particles from the plurality of particles, wherein the isolated particle or particles include one or more candidate aptamer sequences having the desired property; and
    identifying one or more aptamers having the desired property from the isolated particles.

77. A method for identifying a member of an aptamer pair from a mixture of candidate aptamer sequences, the method including:
    immobilizing the mixture of candidate aptamer sequences onto a plurality of particles, wherein only a subset of the candidate aptamer sequences are immobilized on any one of the plurality of particles, and wherein the subset is present in multiple copies;
    exposing a target to an aptamer having a specific binding affinity for the target;

exposing the plurality of particles to the target,
isolating a particle or particles from the plurality of particles, wherein the isolated particle or particles include one or more candidate aptamer sequences which exhibit a specific binding affinity for the target in the presence of the aptamer having a specific binding affinity for the target; and
identifying one or more aptamers from the isolated particles as a member of an aptamer pair which includes the aptamer having a specific binding affinity for the target.

78. The method of 77, wherein the aptamer having a specific binding affinity for the target and/or the target are detectably labeled.

79. The method of 77, wherein the aptamer having a specific binding affinity for the target includes a first detectable label, the target includes a second detectable label, and the first and second detectable labels are different.

80. The method of any one of 76-79, wherein the sequence diversity of the subset of the candidate aptamer sequences immobilized on any one of the plurality of particles is from 1 to $10^6$.

81. The method of 80, wherein the sequence diversity of the subset of the candidate aptamer sequences immobilized on any one of the plurality of particles is from 1 to 100.

82. The method of 81, wherein the sequence diversity of the subset of the candidate aptamer sequences immobilized on any one of the plurality of particles is from 1 to 50.

83. The method of 82, wherein the sequence diversity of the subset of the candidate aptamer sequences immobilized on any one of the plurality of particles is 1.

84. An aptamer screening method, the method including:
exposing a plurality of aptamer particles to a detectably labeled target, wherein
each of the aptamer particles includes multiple copies of a single candidate aptamer sequence bound thereto, and wherein the candidate aptamer sequence bound to each of the plurality of aptamer particles is different;
quantitating a signal for each of the aptamer particles, wherein the signal, when
present, is indicative of a binding interaction between the candidate aptamer sequences bound to each aptamer particle and the detectably labeled target; and
sorting each of the aptamer particles based on the quantitated signal for each aptamer particle.

85. An aptamer screening method, the method including:
exposing a plurality of aptamer particles to a target, wherein each of the aptamer particles includes multiple copies of a single nucleic acid candidate aptamer sequence bound thereto, and wherein the candidate aptamer sequence bound to each of the plurality of aptamer particles is different;
detectably labeling the target to provide a detectably labeled target;
quantitating a signal for each of the aptamer particles, wherein the signal, when
present, is indicative of a binding interaction between the candidate aptamer sequences bound to each aptamer particle and the detectably labeled target; and
sorting each of the aptamer particles based on the quantitated signal for each aptamer particle.

86. The aptamer screening method of 84 or 85, wherein the method includes isolating a subset of the sorted aptamer particles.

87. The aptamer screening method of 86, wherein the method includes identifying one or more aptamer sequences from the candidate aptamer sequences bound to the isolated aptamer particles.

88. The aptamer screening method of any one of 84-87, wherein the method includes an enriching step, wherein the enriching step includes preparing an enriched aptamer particle pool from the isolated subset of the sorted aptamer particles, wherein the enriched aptamer particle pool includes aptamer particles, wherein each of the aptamer particles of the enriched aptamer particle pool includes multiple copies of a single candidate aptamer sequence bound thereto, and wherein the enriched aptamer particle pool has decreased sequence diversity relative to the plurality of aptamer particles from the exposing step.

89. The aptamer screening method of 88, wherein the exposing, quantitating, sorting, isolating, and enriching steps constitute a first round of screening, and the method includes one or more additional rounds of screening, wherein the plurality of aptamer particles for each additional round of screening is the enriched aptamer particle pool from the previous round, and each additional round includes exposing the enriched aptamer particle pool to the detectably labeled target, quantitating a signal for each of the particles in the enriched aptamer particle pool, wherein the signal is indicative of a binding interaction between the candidate aptamer sequences bound to each of the aptamer particles and the detectably labeled target, sorting the aptamer particles based on the quantitated signal, and preparing an enriched aptamer particle pool from the isolated subset of the sorted aptamer particles.

90. The aptamer screening method of 89, wherein the method includes one or more rounds of screening, and wherein following the one or more rounds of screening the identified aptamer sequences are capable of binding the target with a $K_d$ of from about 100 nM to about 100 μM.

91. The aptamer screening method of 90, wherein following the one or more rounds of screening the identified aptamer sequences are capable of binding the target with a $K_d$ of from about 1 μM to about 100 μM.

92. The aptamer screening method of 91, wherein following the one or more rounds of screening the identified aptamer sequences are capable of binding the target with a $K_d$ of from about 1 μM to about 10 μM.

93. The aptamer screening method of 89, wherein the method includes one or more rounds of screening, and wherein following the one or more rounds of screening the identified aptamer sequences are capable of binding the target with a $K_d$ of from about 1 pM to about 100 nM.

94. The aptamer screening method of 93, wherein the identified aptamer sequences are capable of binding the target with a $K_d$ of from about 1 pM to about 10 nM.

95. The aptamer screening method of 94, wherein the identified aptamer sequences are capable of binding the target with a $K_d$ of from about 1 pM to about 5 nM.

96. The aptamer screening method of any one of 84-95, wherein the candidate aptamer sequences include DNA.

97. The aptamer screening method of any one of 84-95, wherein the candidate aptamer sequences include RNA.

98. The aptamer screening method of any one of 84-95, wherein the candidate aptamer sequences include non-natural nucleic acids.

99. The aptamer screening method of any one of 88-95, wherein the candidate aptamer sequences include non-natural nucleic acids and the enriching step includes primer extension.

100. The aptamer screening method of any one of 88-95, wherein the enriching step includes a nucleic acid amplification step.
101. The aptamer screening method of 100, wherein the amplification step includes PCR or reverse transcriptase PCR.
102. The aptamer screening method of any one of 84-101, wherein the detectably labeled target is a fluorescently labeled target.
103. The aptamer screening method of any one of 84-102, wherein each aptamer particle includes a magnetic particle.
104. The aptamer screening method of any one of 84-103, wherein each aptamer particle has at least one dimension of from about 50 nm to about 100 µm.
105. The aptamer screening method of 104, wherein the at least one dimension is from about 50 nm to about 1 µm.
106. The aptamer screening method of 105, wherein the at least one dimension is from about 50 nm to about 500 nm.
107. The aptamer screening method of 106, wherein the at least one dimension is from about 50 nm to about 100 nm.
108. The aptamer screening method of any one of 84-103, wherein the at least one dimension is from about 500 nm to about 100 µm.
109. The aptamer screening method of 108, wherein the at least one dimension is from about 1 µm to about 100 µm.
110. The aptamer screening method of 109, wherein the at least one dimension is from about 50 µm to about 100 µm.
111. The aptamer screening method of any one of 104-110, wherein the at least one dimension is diameter.
112. The aptamer screening method of any one of 84-111, wherein the plurality of aptamer particles includes from about $1 \times 10^2$ to about $1 \times 10^{14}$ aptamer particles.
113. The aptamer screening method of any one of 84-111, wherein the sequence diversity of the plurality of aptamer particles is from about $1 \times 10^2$ to about $1 \times 10^{14}$.
114. The aptamer screening method of any one of 84-113, wherein the signal is related to the binding affinity between the candidate aptamer sequences bound to each of the aptamer particles and the detectably labeled target.
115. The aptamer screening method of any one of 84-114, wherein the sorting step is conducted using Fluorescence Activated Cell Sorting (FACS).
116. The aptamer screening method of any one of 84-115, wherein the sorting step includes separating the aptamer particles using a threshold level for the quantitated signal.
117. The aptamer screening method of 116, wherein the quantitated signal is a fluorescence signal and the threshold level is a fluorescence intensity threshold level.
118. The aptamer screening method of any one of 84-117, wherein each of the aptamer particles of the plurality of aptamer particles includes from about $1 \times 10^2$ to about $1 \times 10^{10}$ candidate aptamer sequences bound thereto.
119. The aptamer screening method of any one of 84-118, wherein the plurality of aptamer particles is prepared using emulsion polymerase chain reaction (PCR).
120. The aptamer screening method of any one of 84-119, wherein the target is a protein target.
121. The aptamer screening method of any one of 84-119, wherein the target is a small molecule target.
122. The aptamer screening method of any one of 84-119, wherein the small molecule target is a toxin.
123. The aptamer screening method of any one of 84-119, wherein the target is a whole cell, a cellular component or a liposome.
124. An aptamer screening method, the method including:
exposing about $1 \times 10^2$ to about $1 \times 10^{14}$ aptamer particles to a fluorescently labeled protein target, wherein each of the aptamer particles includes from about $1 \times 10^2$ to about $1 \times 10^{10}$ copies of a single candidate nucleic acid aptamer sequence bound thereto, and wherein the candidate nucleic acid aptamer sequence bound to each of the plurality of aptamer particles is different;
quantitating a fluorescence signal for each of the aptamer particles, wherein the
signal, when present, is indicative of a binding interaction between the candidate nucleic acid aptamer sequences bound to each aptamer particle and the fluorescently labeled protein target;
sorting each of the aptamer particles based on the quantitated fluorescence signal
for each aptamer particle;
isolating a subset of the sorted aptamer particles; and
identifying one or more nucleic acid aptamer sequences from the candidate nucleic acid aptamer sequences bound to the isolated aptamer particles.
125. An aptamer screening method, the method including:
exposing about $1 \times 10^2$ to about $1 \times 10^{14}$ aptamer particles to a protein target,
wherein each of the aptamer particles includes from about $1 \times 10^2$ to about $1 \times 10^{10}$ copies of a single candidate nucleic acid aptamer sequence bound thereto, and wherein the candidate nucleic acid aptamer sequence bound to each of the plurality of aptamer particles is different;
labeling the protein target to provide a fluorescently labeled protein target;
quantitating a fluorescence signal for each of the aptamer particles, wherein the
signal, when present, is indicative of a binding interaction between the candidate nucleic acid aptamer sequences bound to each aptamer particle and the fluorescently labeled protein target;
sorting each of the aptamer particles based on the quantitated fluorescence signal
for each aptamer particle;
isolating a subset of the sorted aptamer particles; and
identifying one or more nucleic acid aptamer sequences from the candidate nucleic acid aptamer sequences bound to the isolated aptamer particles.
126. The aptamer screening method of 124 or 125, wherein the method includes an enriching step, wherein the enriching step includes preparing an enriched aptamer particle pool from the isolated subset of the sorted aptamer particles, wherein the enriched aptamer particle pool includes aptamer particles, wherein each of the aptamer particles of the enriched aptamer particle pool includes multiple copies of a single candidate nucleic acid aptamer sequence bound thereto, and wherein the enriched aptamer particle pool has decreased sequence diversity relative to the plurality of aptamer particles from the exposing step.
127. The aptamer screening method of 126, wherein the exposing, quantitating, sorting, isolating, and enriching steps constitute a first round of screening, and the method includes one or more additional rounds of screening, wherein the plurality of aptamer particles for each additional round of screening is the enriched aptamer particle pool from the previous round, and each additional round includes exposing the enriched aptamer particle pool to the fluorescently labeled protein target, quantitating a fluorescence signal for each of the particles in the enriched aptamer particle pool, wherein the signal is indicative of a binding interaction between the candidate nucleic acid aptamer sequences bound to each of the aptamer particles and the fluorescently labeled protein target, sorting the aptamer particles based on the quantitated fluorescence signal, and preparing an enriched aptamer particle pool from the isolated subset of the sorted aptamer particles.

128. The aptamer screening method of 126, wherein the exposing, labeling, quantitating, sorting, isolating, and enriching steps constitute a first round of screening, and the method includes one or more additional rounds of screening, wherein the plurality of aptamer particles for each additional round of screening is the enriched aptamer particle pool from the previous round, and each additional round includes exposing the enriched aptamer particle pool to the protein target, labeling the protein target to provide a fluorescently labeled protein target, quantitating a fluorescence signal for each of the particles in the enriched aptamer particle pool, wherein the signal is indicative of a binding interaction between the candidate nucleic acid aptamer sequences bound to each of the aptamer particles and the fluorescently labeled protein target, sorting the aptamer particles based on the quantitated fluorescence signal, and preparing an enriched aptamer particle pool from the isolated subset of the sorted aptamer particles.

129. The aptamer screening method of 127 or 128, wherein the method includes one or more rounds of screening, and wherein following the one or more rounds of screening the identified aptamer sequences are capable of binding the protein target with a $K_d$ of from about 1 pM to about 10 nM.

130. An aptamer screening method, the method including:
preparing a library of aptamer particles using emulsion PCR, wherein the library
includes about $1\times10^2$ to about $1\times10^{14}$ aptamer particles;
exposing the library to a detectably labeled protein target, wherein each of the aptamer particles includes from about $1\times10^2$ to about $1\times10^{10}$ copies of a single candidate nucleic acid aptamer sequence bound thereto, and wherein the candidate nucleic acid aptamer sequence bound to each of the plurality of aptamer particles is different;
quantitating a fluorescence signal for each of the aptamer particles using fluorescence activated cell sorting (FACS), wherein the signal, when present, is indicative of a binding affinity between the candidate nucleic acid aptamer sequences bound to each aptamer particle and the fluorescently labeled protein target;
sorting each of the aptamer particles based on the quantitated fluorescence signal
for each aptamer particle;
isolating a subset of the sorted aptamer particles; and
identifying one or more nucleic acid aptamer sequences from the candidate nucleic acid aptamer sequences bound to the isolated aptamer particles.

131. A pool of aptamer particles, the pool including aptamer particles including aptamer sequences capable of binding a target, the pool of aptamer particles including:
from about $1\times10^2$ to about $1\times10^{14}$ aptamer particles,
wherein each aptamer particle of the pool of aptamer particles includes from about $1\times10^2$ to about $1\times10^{10}$ copies of a single nucleic acid aptamer sequence bound thereto,
wherein the sequence diversity of the pool of aptamer particles is less than the number of aptamer particles in the pool,
wherein each of the aptamer particles has at least one dimension of from about 50 nm to about 100 μm, and
wherein a plurality of the aptamer particles include aptamer sequences bound thereto which are capable of binding the target with a $K_d$ of from about 1 pM to about 100 μM.

132. The pool of aptamer particles of 131, wherein the $K_d$ is from about 100 nM to about 100 μM.

133. The pool of aptamer particles of 131, wherein the $K_d$ is from about 1 μM to about 100 μM.

134. The pool of aptamer particles of 133, wherein the $K_d$ is from about 1 μM to about 10 μM.

135. The pool of aptamer particles of 131, wherein the $K_d$ is from about 1 pM to about 100 nM.

136. The pool of aptamer particles of 135, wherein the $K_d$ is from about 1 pM to about 10 nM.

137. The pool of aptamer particles of 136, wherein the $K_d$ is from about 1 pM to about 5 nM.

138. The pool of aptamer particles of any one of 131-137, wherein the aptamer sequences include DNA.

139. The pool of aptamer particles of any one of 131-137, wherein the aptamer sequences include RNA.

140. The pool of aptamer particles of any one of 131-137, wherein the aptamer sequences include non-natural nucleic acids.

141. The pool of aptamer particles of any one of 131-140, wherein the pool of aptamer particles is in an emulsion.

142. The pool of aptamer particles of any one of 131-141, wherein each aptamer particle includes a magnetic particle.

143. The pool of aptamer particles of 131-142, wherein the at least one dimension is from about 50 nm to about 1 μm.

144. The pool of aptamer particles of 143, wherein the at least one dimension is from about 50 nm to about 500 nm.

145. The pool of aptamer particles of 144, wherein the at least one dimension is from about 50 nm to about 100 nm.

146. The pool of aptamer particles of any one of 131-142, wherein the at least one dimension is from about 500 nm to about 100 μm.

147. The pool of aptamer particles of 146, wherein the at least one dimension is from about 1 μm to about 100 μm.

148. The pool of aptamer particles of 147, wherein the at least one dimension is from about 50 μm to about 100 μm.

149. The pool of aptamer particles according to any one of 131-148, wherein the at least one dimension is diameter.

150. The pool of aptamer particles according to any one of 131-149, wherein the target is a protein.

151. An isolated aptamer including the sequence set forth in any one of SEQ. ID. NOs. 1-20.

152. An isolated aptamer including the sequence set forth in any one of SEQ. ID. NOs. 21-40.

153. An isolated aptamer including the sequence set forth in any one of SEQ. ID. NOs. 41-60.

154. An isolated aptamer including the sequence set forth in any one of SEQ. ID. NOs. 61-80.

155. An aptamer particle library, including:
from about $1\times10^2$ to about $1\times10^{14}$ aptamer particles,
wherein each aptamer particle of the aptamer particle library includes from about $1\times10^2$ to about $1\times10^{10}$ copies of a single candidate nucleic acid aptamer sequence bound thereto, and wherein the candidate aptamer sequence bound to each of the of the aptamer particles of the aptamer particle library is different.

156. The aptamer particle library of 155, wherein the candidate nucleic acid aptamer sequences include DNA.
157. The aptamer particle library of 155, wherein the candidate nucleic acid aptamer sequences include RNA.
158. The aptamer particle library of 155, wherein the candidate nucleic acid aptamer sequences include non-natural nucleic acids.
159. The aptamer particle library of 155, wherein each aptamer particle includes a magnetic particle.
160. The aptamer particle library of 155, wherein each aptamer particle has at least one dimension of from about 50 nm to about 100 μm.
161. The aptamer particle library of 160, wherein the at least one dimension is from about 50 nm to about 1 μm.
162. The aptamer particle library of 161, wherein the at least one dimension is from about 50 nm to about 500 nm.
163. The aptamer particle library of 162, wherein the at least one dimension is from about 50 nm to about 100 nm.
164. The aptamer particle library of 155, wherein the at least one dimension is from about 500 nm to about 100 μm.
165. The aptamer particle library of 164, wherein the at least one dimension is from about 1 μm to about 100 μm.
166. The aptamer particle library of 165, wherein the at least one dimension is from about 50 μm to about 100 μm.
167. The aptamer particle library of any one of 160-166, wherein the at least one dimension is diameter.

BRIEF DESCRIPTION OF THE DRAWINGS

FIG. 1 provides a general overview of one round of an aptamer particle generation and screening method according to the present disclosure, including the following steps (1) populating APs with candidate aptamer sequences; (2) exposing APs to a target, e.g., a detectably labeled target; (3) quantitatively sorting APs based on an interaction between the candidate aptamer sequences displayed on the surface of the APs and the target; and (4) enriching for selected candidate aptamer sequences. Steps (1)-(4) may be repeated one or more times to facilitate isolation and identification of aptamers having desired target interactions.

FIG. 2 provides a more detailed depiction of one round of an aptamer screening method according to some embodiments of the present disclosure. APs are synthesized by emulsion PCR (step 1-3), incubated with fluorescently labeled target molecules (step 4) and quantitatively screened by FACS (step 5) based on fluorescence intensity. Isolated AP-displayed aptamers are then PCR-amplified to generate an enriched pool (step 6), which is used for synthesizing APs for the next round of screening or sequencing (step 7).

FIGS. 9A and 9B: Selected aptamer sequences. To obtain individual aptamer sequences, the R3 pools were cloned into competent bacterial cells and 20 clones were randomly picked and sequenced from each. The clone sequences are shown in Tables 1-5 and in FIGS. 9A and 9B (From top to bottom: Thrombin 01-16 SEQ ID NO:1; Thrombin 03-20

Figure 1:
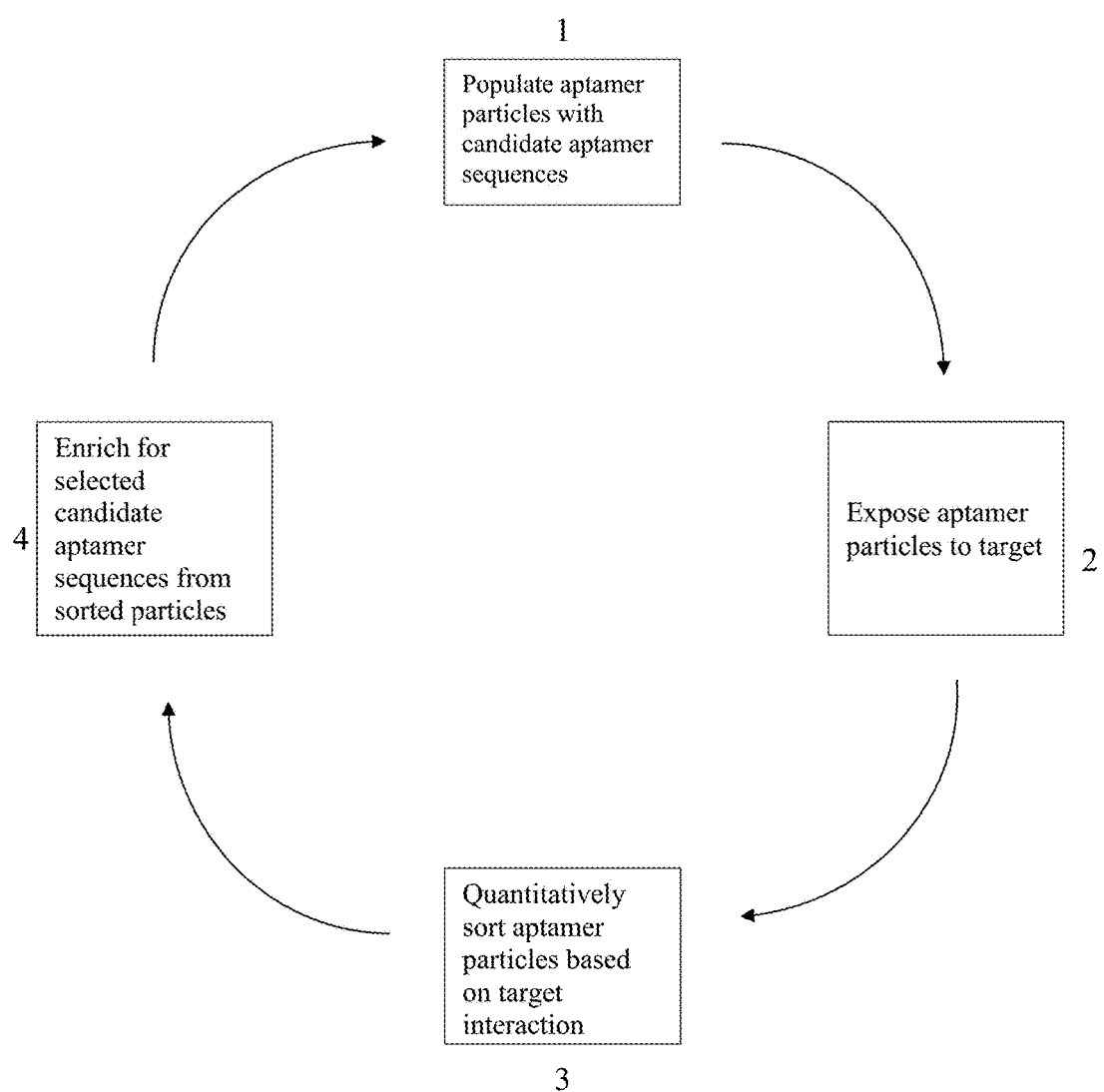
FIG. 1.

SEQ ID NO: 2; Thrombin 06-18 SEQ ID NO:3; Thrombin 09 SEQ ID NO:4; Thrombin 10 SEQ ID NO:5; ApoE 01-09 SEQ ID NO:6; ApoE 02-017 SEQ ID NO:7; ApoE 20 SEQ ID NO:9; ApoE 03-15 SEQ ID NO:8; ApoE 06-19 SEQ ID NO:9; PAI-1 01-19 SEQ ID NO:10; PAI-1 04-16 SEQ ID NO:12; PAI-1 03-20 SEQ ID NO:11; PAI-1 06 SEQ ID NO:13; 4-1BB 01-15 SEQ ID NO:14; 4-1BB 07-20 SEQ ID NO:18; 4-1BB 04-16 SEQ ID NO:16; 4-1BB 03-13 SEQ ID NO:15; 4-1BB 05 SEQ ID NO:17).

DEFINITIONS

As used herein the term "candidate nucleic acid agent" refers to a nucleic acid intended for use in a nucleic acid screening method.

As used herein the term "nucleic acid agent" refers to a nucleic acid having a desired property.

As used herein the term "candidate aptamer" or "candidate aptamer sequence" refers to a nucleic acid member of a library intended for use in an aptamer screening method.

As used herein the term "aptamer" or "aptamer sequence" refers to a nucleic acid having a specific binding affinity for a target, e.g., a target molecule, wherein such target is other than a polynucleotide that binds to the aptamer or aptamer sequence through a mechanism which predominantly depends on Watson/Crick base pairing.

The terms "nucleic acid", "nucleic acid sequence", "nucleic acid molecule" and "polynucleotide" may be used interchangeably herein and refer to a polymeric form of nucleotides of any length, either deoxyribonucleotides or ribonucleotides, or analogs thereof, and may include naturally occurring nucleotides and/or modified nucleotides. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

The terms "peptide", "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The term "sequence" as used, for example, in the context of an aptamer sequence, a candidate aptamer sequence, a nucleic acid sequence or an amino acid sequence may refer to the primary structure, e.g., the order of monomeric subunits, e.g., nucleotides or amino acids, and/or to the molecule having the primary structure.

The terms "antibody" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins including an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies.

Antibodies may exist in a variety of other forms including, for example, Fv, Fab, and (Fab')$_2$, as well as bi-functional (i.e. bi-specific) hybrid antibodies (e.g., Lanzavecchia et al., *Eur. J. Immunol.* 17, 105 (1987)) and in single chains (e.g., Huston et al., *Proc. Natl. Acad. Sci. U.S.A.*, 85, 5879-5883 (1988) and Bird et al., Science, 242, 423-426 (1988), which are incorporated herein by reference). (See, generally, Hood et al., "*Immunology*", Benjamin, N.Y., 2nd ed. (1984), and Hunkapiller and Hood, Nature, 323, 15-16 (1986),).

Chimeric antibodies are antibodies whose light and heavy chain genes have been constructed, typically by genetic engineering, from antibody variable and constant region genes belonging to different species. For example, the variable segments of the genes from a rabbit monoclonal antibody may be joined to human constant segments, such as gamma 1 and gamma 3. An example of a therapeutic chimeric antibody is a hybrid protein composed of the variable or antigen-binding domain from a rabbit antibody and the constant or effector domain from a human antibody (e.g., the anti-Tac chimeric antibody made by the cells of A.T.C.C. deposit Accession No. CRL 9688), although other mammalian species may be used.

The terms "label" and "detectable label" may be used interchangeably herein to refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, strepavidin or haptens) and the like. Exemplary detectable moieties suitable for use as detectable labels include affinity tags and fluorescent proteins.

The term "fluorescer" refers to a substance or a portion thereof which is capable of exhibiting fluorescence in the detectable range.

The term "affinity tag" is used herein to denote a peptide segment that can be attached to a target that can be detected using a molecule that binds the affinity tag and provides a detectable signal (e.g., a fluorescent compound or protein). In principal, any peptide or protein for which an antibody or other specific binding agent is available can be used as an affinity tag.

"Stringency conditions" refers to conditions in a reaction mixture that influence formation of complexes between candidate nucleic acid agents, e.g., aptamer sequences, and a target. Additional stringency conditions are described, for example, in U.S. Application Publication No. 2009/0170718, the disclosure of which is incorporated by reference herein in its entirety and for all purposes.

The term "reaction mixture" as used herein refers to a fluid medium in which a target is contacted with or in contact with candidate nucleic acid agents, e.g., candidate aptamer sequences. This includes, for example, a reaction mixture in which a library of candidate nucleic acid agents, e.g., aptamer sequences, is initially contacted with a target and any subsequent wash steps designed to remove non-specific or low-affinity target binding agents. Where desired, the stringency conditions of the reaction mixture can be modified so as to influence the formation of complexes between the target and the candidate nucleic acid agents, e.g., candidate aptamer sequences. Thus, for example, stringency conditions of a reaction mixture during initial contacting of target and a library of candidate nucleic acid agents, e.g., candidate aptamer sequences, (which may be referred to as "binding conditions") and stringency conditions of a reaction mixture during washing (referred to as "wash conditions", e.g., to disrupt complexes of an undesirably low affinity and/or deplete non-specifically bound candidate nucleic acid agents) may be of the same or different stringencies.

The terms "specific binding," "specifically bind," and the like, refer to the ability of a first binding molecule or moiety to preferentially bind (covalently or non-covalently) to a second binding molecule or moiety relative to other molecules or moieties in a reaction mixture.

As used herein, a "member of a specific binding pair" is a member of a specific binding pair interaction. It should be noted that when either member of the binding pair is referred to as the first member, the remaining member is understood to be the second member and vice versa. Examples of specific binding pair interactions include immune binding interactions such as antigen/antibody and hapten/antibody as well as non-immune binding interactions such as complementary nucleic acid binding, biotin/avidin and biotin/streptavidin.

As used herein, the terms "determining," "measuring," "assessing," and "assaying" are used interchangeably and include both quantitative and qualitative determinations unless the context clearly indicates otherwise.

The term "member of a reactive pair" is used herein to refer to first or second functional group, wherein the first and second functional groups react with one another under suitable conditions to form a covalent bond. Such reactive pairs may also be referred to as "covalent bond forming reactive pairs." It should be noted that when either member of the reactive pair is referred to as the first member, the remaining member is understood to be the second member and vice versa. Examples of first and second members of covalent bond forming reactive pairs include Cu-catalyzed azide/alkyne[3+2] cycloaddition "Click Chemistry" as described by Rostovtsev et al. (2002) *Angew. Chem. Int. Ed.* 41: 2596-2599 and Tornoe et al. (2002) *J. Org. Chem.* 67: 3057-3064; azide/DIFO (Difluorinated Cyclooctyne) Cu-free Click Chemistry as described by Baskin et al. (2007) *PNAS* Vol. 104, No. 43: 167393-16797; azide/phosphine "Staudinger Reaction" as described by Lin et al. (2005) *J. Am. Chem. Soc.* 127: 2686-2695; azide/triarylphosphine "Modified Staudinger Reaction" as described by Saxon and Bertozzi (2000) March 17 *Science* 287(5460):2007-10; and catalyzed olefin cross metathesis reactions as described by Casey (2006) *J. of Chem. Edu.* Vol. 83, No. 2: 192-195, Lynn et al. (2000) *J. Am. Chem. Soc.* 122: 6601-6609, and Chen et al. (2003) *Progress in Chemistry* 15: 401-408.

In some embodiments, "click chemistry functional groups" are of interest as first and second members of a reactive pair. The term "click chemistry function group" refers to an azide functional group or an alkyne functional group capable of participating in a covalent bond forming reaction with an alkyne function group or an azide functional group respectively. The term "click chemistry functional group" is also used herein to refer to an azide functional group or a DIFO functional group capable of participating in a covalent bond forming reaction with a DIFO functional group or an azide functional group respectively. It should be noted that while the azide/alkyne covalent bond forming reaction requires the presence of a Cu ion catalyst, the azide/DIFO covalent bond forming reaction does not require the use of such a catalyst.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the present disclosure. The upper and lower limits of these smaller ranges may independently be included in the smaller ranges, and are also encompassed within the present disclosure, subject to any specifically excluded limit in the stated range. Where the stated range includes one or both of the limits, ranges excluding either or both of those included limits are also included in the present disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the disclosed methods, compositions and systems, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "an aptamer particle" includes a plurality of such aptamer particles and reference to "the candidate aptamer sequence" includes reference to one or more candidate aptamer sequences and equivalents thereof known to those skilled in the art, and so forth. It is further noted that the claims may be drafted to exclude any disclosed element. As such, this statement is intended to serve as antecedent basis for use of such exclusive terminology as "solely," "only" and the like in connection with the recitation of claim elements, or use of a "negative" limitation.

To the extent the disclosure, e.g., the definition or usage of any term herein, conflicts with a disclosure, e.g., a definition or usage of a term, in an application or reference incorporated by reference herein, the instant application shall control.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order which is logically possible. This is intended to provide support for all such combinations.

DETAILED DESCRIPTION

As discussed above, the present disclosure provides a method for identifying one or more nucleic acid agents, e.g., aptamers, having a desired property from a mixture of candidate nucleic acid agents. The method generally includes immobilizing the mixture of candidate nucleic acid agents onto particles, wherein only a subset of the candidate nucleic acid agents are immobilized on any one of the particles, and wherein the subset is present in multiple copies. The particles are exposed to a target, and particles including candidate nucleic acid agents having the desired property are isolated. In this way, one or more nucleic acid agents having the desired property may be identified.

The present disclosure also provides a quantitative, particle based method of generating and screening candidate aptamers. Generally, a library of aptamer particles (APs) is prepared, wherein each AP displays multiple copies of a unique candidate aptamer sequence on its surface. The APs are exposed to a target and each AP is sorted based on a quantitative analysis of an interaction between the candidate aptamer sequences on the AP and the target. Following sorting, an enriched pool of aptamer particles may be provided which has reduced sequence diversity relative to the original library. One or more rounds of screening may be performed to identify aptamers having desired target interactions. This method is depicted generally in FIG. 1.

Synthesis of Particle-Immobilized Candidate Nucleic Acid Agents and Aptamer Particles (Ap)

Candidate Nucleic Acid Agents and Candidate Aptamers

Suitable candidate nucleic acid agents and candidate aptamers for use in connection with the disclosed methods and compositions include nucleic acids, e.g., single stranded nucleic acids. Candidate nucleic acid agents and candidate aptamers may be provided in the form of combinatorial candidate nucleic acid agent and candidate aptamer libraries respectively which include a large number of at least partially random nucleic acid sequences. Candidate nucleic acid agent libraries and candidate aptamer libraries may include, for example, from about $1 \times 10^2$ to about $1 \times 10^{14}$ unique candidate nucleic acid agent sequences and from about $1 \times 10^2$ to about $1 \times 10^{14}$ unique candidate aptamer sequences respectively, e.g., from about $1 \times 10^3$ to about $1 \times 10^{14}$ unique sequences, from about $1 \times 10^4$ to about $1 \times 10^{14}$ unique sequences, from about $1 \times 10^5$ to about $1 \times 10^{14}$ unique sequences, from about $1 \times 10^6$ to about $1 \times 10^{14}$ unique sequences, from about $1 \times 10^7$ to about $1 \times 10^{14}$ unique sequences, from about $1 \times 10^8$ to about $1 \times 10^{14}$ unique sequences, from about $1 \times 10^9$ to about $1 \times 10^{14}$ unique sequences, from about $1 \times 10^{10}$ to about $1 \times 10^{14}$ unique sequences, from about $1 \times 10^{11}$ to about $1 \times 10^{14}$ unique sequences, from about $1 \times 10^{12}$ to about $1 \times 10^{14}$ unique sequences, or from about $1 \times 10^{13}$ to about $1 \times 10^{14}$ unique sequences.

Candidate nucleic acid agents and candidate aptamers including nucleic acid sequences suitable for use in connection with the disclosed methods and compositions may be, for example, from about 30 to about 150 nucleotides in length, e.g., from about 40 to about 130 nucleotides in length, from about 50 to about 120 nucleotides in length, from about 60 to about 110 nucleotides in length, from about 70 to about 100 nucleotides in length, or from about 80 to about 90 nucleotides in length. Candidate nucleic acid agents and candidate aptamers including nucleic acid sequences may include random nucleic acid sequences of from about 30 nucleotides in length to about 70 nucleotides in length, e.g., from about 40 nucleotides in length to about 60 nucleotides in length. In addition to random nucleic acid sequence regions, candidate nucleic acid agents and candidate aptamers including nucleic acid sequences may include flanking regions containing primer binding sites.

Candidate nucleic acid agents and candidate aptamers including nucleic acid sequences suitable for use in connection with the disclosed methods and compositions may include deoxyribonucleotides, ribonucleotides, or analogs thereof, and may include naturally occurring nucleotides and/or modified nucleotides. For example, candidate nucleic acid agents and candidate aptamers including nucleic acid sequences suitable for use in connection with the disclosed methods and compositions may include 2'-fluoro-modified RNA, 2'-O-methyl-modified RNA, and chemically modified DNA.

Particles

A variety of suitable particles may be used in the generation of particle-immobilized nucleic acids and aptamer particles as described herein. Such particles may be sized to have at least one dimension, e.g., diameter, of from about 50 nm to about 100 µm. For example, in some embodiments a suitable particle is sized to have at least one dimension of from about 50 nm to about 1 µm, e.g., from about 50 nm to about 500 nm, or from about 50 nm to about 100 nm. In other embodiments, a suitable particle is sized to have at least one dimension of from about 500 nm to about 100 µm, e.g., from about 1 µm to about 100 µm, or from about 50 µm to about 100 µm. Suitable particles may be generally spherical or may have any other suitable shape.

Particles may be made from a variety of suitable materials known in the art. For example, magnetic particles may be utilized in the disclosed methods and compositions. Suitable magnetic particles may include, for example, magnetic beads or other small objects made from a magnetic material such as a ferromagnetic material, a paramagnetic material, or a superparamagnetic material. Magnetic particles may include, e.g., iron oxide ($Fe_2O_3$ and/or $Fe_3O_4$). Additional particles of interest may include polymer based particles, e.g., polymer based beads. For example, polystyrene particles may be utilized. In addition, in some embodiments ceramic particles may be utilized.

The particles may include or be coated with a material which facilitates coupling of the particles to candidate nucleic acid agents and candidate aptamer sequences. Examples of coatings include polymer shells, glasses, ceramics, gels, etc. In some embodiments, the coatings include or are themselves coated with a material that facilitates coupling or physical association of the particles with the candidate nucleic acid agent sequences and candidate aptamer sequences. For example, particles with exposed carboxylic acid groups may be used for attachment to candidate nucleic acid agents and candidate aptamers.

Suitable particles may include one or more functional groups, e.g., one or members of a reactive pair as described herein, positioned on one or more surfaces of the particles. Suitable functional groups may include, for example, amine groups, carboxyl groups, thiol groups, $SiO_2$, EDTA, and boronic acid functional groups.

In some embodiments, suitable particles may include one or more members of a specific binding pair on one or more surfaces of the particles. For example, avidin, streptavidin, Neutravidin®, Captavidin™, or biotin may be positioned on one or more surfaces of the particles.

Methods of Attaching Candidate Nucleic Acid Agents and Candidate Aptamer Sequences to Particles A variety of methods may be used to attach candidate nucleic acid agents and candidate aptamer sequences, such as those described above, to particles to make particle-immobilized candidate nucleic acid agents and aptamer particles as described herein.

In one suitable method, candidate nucleic acid agent sequences or candidate aptamer sequences may be attached to a particle having exposed carboxylic acid groups using amino group modification. For example, 5'-amino modified oligonucleotides may be used in connection with carbodiimide mediated amide bond formation to attach candidate nucleic acid agent sequences or candidate aptamer sequences to particles.

Carbodiimide mediated coupling methods are described in greater detail, for example, in Nakajima N. and Ikade Y. (1995) *Bioconjugate Chem.*, 6(1):123-130; Gilles et al. (1990) *Anal Biochem.*, 184(2):244-248; Sehgal D. and Vijay IK. (1994) *Anal Biochem.* 218(1):87-91; and Szajani et al. (1991) *Appl Biochem Biotechnol.* 30(2):225-231.

Where primer based enrichment methods such as PCR, reverse transcriptase

PCR, or primer extension are utilized to provide a library of particle-immobilized candidate nucleic acid agents or an aptamer particle library, nucleic acid primers may be attached to particles using carbodiimide mediated coupling to facilitate these methods. For example, the coupling of 5'-amino-modified forward primers in described in greater detail in Example 1 below. Amino group modification may be beneficial, for example, because this coupling is covalent and can keep primers attached to the particles during thermal cycling. Alternatively, biotin labeled primers may be utilized with streptavidin-coated particles to provide primer-coated beads.

Particle-Immobilized Candidate Nucleic Acid Agent Library Synthesis and Aptamer Particle Library Synthesis Suitable methods for the synthesis of libraries of particle-immobilized candidate nucleic acid agents and aptamer particles, including candidate DNA nucleic acid agents and candidate DNA aptamer sequences respectively, include, for example, emulsion PCR. Generally, emulsion PCR as used in connection with the disclosed methods isolates individual template DNA molecules, e.g., from a combinatorial library, along with primer-coated particles, e.g., beads, in aqueous droplets within an oil phase. PCR amplification then coats each bead with clonal copies of the DNA molecule. After breaking the emulsion and removing unreacted PCR reagents, hybridized strands may be de-hybridized and the aptamer particles collected for subsequent screening. A detailed description of one embodiment of an emulsion PCR method is provided in Example 1 below.

Where the candidate nucleic acid agent sequences or candidate aptamer sequences include RNA sequences, a modified version of the emulsion PCR method may be utilized. For example, a random DNA library may be synthesized, which represents the template of the candidate RNA nucleic acid agents or the candidate RNA aptamers. The DNA library can be paired with a complementary primer sequence and the reverse strand can be extended to form a double-stranded library which can initiate transcription. An emulsion can be prepared with the library, the transcription reagents, and a particle coated with sequences that can hybridize with the RNA transcripts by base-pairing. The emulsion can be prepared such that each emulsion droplet will only contain one or a few DNA templates, and the RNA transcript from that one or a few templates will be captured by the respective particles to form a particle-immobilized candidate RNA nucleic acid agent library or an RNA aptamer particle library.

In another approach, particle-immobilized candidate DNA nucleic acid agents or DNA aptamer particles can be synthesized as described previously herein using emulsion PCR. Then, a second emulsion can be prepared with the particle-immobilized candidate DNA nucleic acid agents or DNA aptamer particles, transcription reagents, and a second set of particles that contain sequences that can hybridize with RNA by base-pairing. The emulsion can be prepared such that each emulsion droplet will only contain one or a few particle-immobilized candidate DNA nucleic acid agents or DNA aptamer particles and their corresponding RNA transcripts. The RNA transcripts can be captured by the second set of particles to form a particle-immobilized candidate RNA nucleic acid agent library or an RNA aptamer particle library.

Where the candidate aptamer sequences include non-natural nucleic acids, a modified version of the emulsion PCR method may be utilized. For example, in a first step, starting from a non-natural nucleic acid sequence as template, a DNA primer sequence and natural A/T/C/G building blocks are used to PCR amplify the sequence into an amplified pool of natural DNA sequences (the amplified DNA will have the same sequence as the template, but not the non-natural composition). In order to obtain amplified non-natural nucleic acid sequences on particles, the natural DNA sequences derived from first step can be used as template in an emulsion reaction. A primer positioned on the particles can be used to pair with the template, and a polymerase capable of incorporating non-natural nucleic acids can be used to incorporate non-natural nucleic acid building blocks to extend the primer to a full-length complementary sequences. Suitable polymerases are known in the art. In addition, methods of identifying such polymerases are known in the art. See, for example, Lutz et al. *Nucleic Acids Research,* 1999, Vol. 27, No. 13, pp. 2792-2798, the disclosure of which is incorporated by reference herein.

Screening of Particle-Immobilized Candidate Nucleic Acid Agents and Aptamer Particles Generally, a particle-immobilized candidate nucleic acid agent screening method according to the present disclosure includes identifying one or more nucleic acid agents having a desired property from a mixture of candidate nucleic acid agents. In some embodiments, the method includes immobilizing the mixture of candidate nucleic acid agents onto particles, wherein only a subset of the candidate nucleic acid agents are immobilized on any one of the particles, and wherein the subset is present in multiple copies. The particles are exposed to a target, and particles including candidate nucleic acid agents having the desired property are isolated. In this way, one or more nucleic acid agents having the desired property may be identified.

The desired property may be a target binding activity or a target-binding induced activity, e.g., a catalytic activity or a modified catalytic activity; inhibition activity, activation activity, or a modification of an inhibition activity or activation activity; structure switching activity or a modification of a structure switching activity; or cooperative activity.

In some embodiments, the isolating step includes contacting the plurality of particles with one or more detectable labels, wherein the one or more detectable labels associate to a higher level with particles including one or more candidate nucleic acid agents having the desired property and associate to a lower level with particles which do not include one or more candidate nucleic acid agents having the desired property. Alternatively, the isolating step may include contacting the plurality of particles with one or more detectable labels, wherein the one or more detectable labels associate to a lower level with particles including one or more candidate nucleic acid agents having the desired property and associate to a higher level with particles which do not include one or more candidate nucleic acid agents having the desired property.

In some embodiments, the method includes a step of quantitating a signal from the detectable labels. In some embodiments, the method includes a step of enriching a population of the plurality of particles based on the quantitated signal. In some embodiments, the method includes a step of introducing one or more mutations into one or more candidate nucleic acid agents or into one or more nucleic acid agents having the desired property.

In some embodiments, the method includes iteratively repeating one or more of the immobilizing, exposing, isolating and identifying steps described above. In some embodiments, the method includes iteratively repeating one or more of the contacting, enriching, and introducing steps described above. The method may include, for example, a total of 1, 2, 3, 4 or more rounds of screening.

As discussed above, in some embodiments, the desired property is a target binding activity or a target-binding induced activity. In some embodiments, the target binding activity is one of affinity, specificity and bi-specificity.

In one such embodiment, the target binding activity is specificity, and the screening method includes a step of exposing the plurality of particles to a first target and a second target. Nucleic acid agents having the desired property will exhibit a specific binding affinity (e.g, a $K_d$ of from about 1 pM to about 100 nM, e.g., a $K_d$ of from about 1 pM to about 10 nM, or a $K_d$ of from about 1 pM to about 5 nM) for either the first target or the second target but not both. For example, the first target may be a first homolog or splicing variant of a protein and the second target may be a second homolog or splicing variant of the protein. In another embodiment, the first target may be a first post-translational modification form of a protein and the second target may be a second post-translation modification form of a protein. In another embodiment, the first target may be a protein which has been subjected to a post-translational modification and the second target may be a form of the protein which has not been subjected to the post-translational modification. For example, a nucleic acid agent having the desired property may bind to a phosphorylated form of a protein but not the unphosphorylated form or vice versa.

A variety of post-translational modifications are known in the art, e.g., myristoylation, palmitoylation, isoprenylation or prenylation, glypiation, lipoylation, the addition of flavin, the addition of heme C, phosphopantetheinylation, retinylidene Schiff base formation, acylation (e.g., acetylation), alkylation (e.g., methylation), amide bond formation, glycosylation, nucleotide addition, oxidation, phosphate ester (O-linked) or phosphoramidate (N-linked) formation (e.g., phosphorylation and adenylylation), glycation, biotinylation and PEGylation, among others.

In some embodiments, the first target is a first conformational form of a protein and the second target is a second conformational form of the protein. For example, the first target may be a ligand-bound form of an enzyme and the second target may be an unbound form of the same enzyme or vice versa.

In some embodiments, the target binding activity is bi-specificity. In such embodiments, the screening method may include a step of exposing the plurality of particles to a first target and a second target. Nucleic acid agents having the desired property will exhibit a specific binding affinity (e.g, a $K_d$ of from about 1 pM to about 100 nM, e.g., a $K_d$ of from about 1 pM to about 10 nM, or a $K_d$ of from about 1 pM to about 5 nM) for both the first and second target. In such embodiments, the first target may be a first homolog or splicing variant of a protein and the second target may be a second homolog or splicing variant of the protein. The first target may be a first post-translational modification form of a protein and the second target may be a second post-translation modification form of a protein, e.g., as described above. In addition, the first target may be a protein which has been subjected to a post-translational modification and the second target may be a form of the protein which has not been subjected to the post-translational modification, e.g., as described above. The first target may be a first conformational form of a protein and the second target may be a second conformational form of the protein, e.g., as described above.

In some embodiments, multiple detectable labels may be used to facilitate the screening process. For example, where the target binding activity is specificity, the screening method may include exposing the plurality of particles to a first target labeled with a first detectable label and a second target labeled with a second detectable label, wherein the first detectable label and the second detectable label are different. Nucleic acid agents having the desired property will exhibit a first binding affinity for the first target and a second binding affinity for the second target, wherein the first binding affinity and the second binding affinity are significantly different. These binding affinities may be determined via detection of the detectable labels. For example, in order to screen for aptamers that specifically bind to a thrombin protein in serum, thrombin can be labeled with a first detectable label while all other serum proteins are labeled with a second, different detectable label. Aptamers associated with a relatively high signal from the first detectable label, which is indicative of relatively high affinity thrombin binding, and a relatively low signal from the second detectable label, which is indicative of relatively low affinity binding to other serum proteins, may be selected.

Similarly, multiple detectable labels may be used where the target binding activity is bi-specificity. For example, the screening method may include exposing the plurality of particles to a first target labeled with a first detectable label and a second target labeled with a second detectable label, wherein the first detectable label and the second detectable label are different. Nucleic acid agents having the desired property will exhibit a specific binding affinity (e.g, a $K_d$ of from about 1 pM to about 100 nM, e.g., a $K_d$ of from about 1 pM to about 10 nM, or a $K_d$ of from about 1 pM to about 5 nM) for both the first and second target, which binding affinity may be determined via detection of the detectable labels.

In some embodiments, an aptamer screening method according to the present disclosure includes at least the following steps: (1) exposing a plurality of aptamer particles to a detectably labeled target, wherein each of the aptamer particles includes multiple copies of a single candidate aptamer sequence bound thereto, and wherein the candidate aptamer sequence bound to each of the plurality of aptamer particles is different; (2) quantitating a signal for each of the aptamer particles, wherein the signal, when present, is indicative of a binding interaction between the candidate aptamer sequences bound to each aptamer particle and the detectably labeled target; and (3) sorting each of the aptamer particles based on the quantitated signal for each aptamer particle. In some embodiments, the target is detectably labeled to provide the detectably labeled target before exposure to the plurality of aptamer particles. In other embodiments, the target is detectably labeled to provide the detectably labeled target after exposure to the plurality of aptamer particles. In some embodiments, the target is inherently detectable without the addition of a label and no labeling is required.

In addition to the above steps, the aptamer screening method may include steps of (4) isolating a subset of the sorted aptamer particles and (5) identifying one or more aptamer sequences from the candidate aptamer sequences bound to the isolated aptamer particles.

The method may also include an enriching step, wherein the enriching step includes preparing an enriched aptamer particle pool from the isolated subset of the sorted aptamer particles, wherein the enriched aptamer particle pool includes aptamer particles, wherein each of the aptamer particles of the enriched aptamer particle pool includes multiple copies of a single candidate aptamer sequence bound thereto, and wherein the enriched aptamer particle pool has decreased sequence diversity relative to the plurality of aptamer particles from the exposing step.

In some embodiments, the exposing, quantitating, sorting, isolating, and enriching steps discussed above may constitute a first round of screening. The method may include one or more additional rounds of screening, e.g., two, three or four additional rounds of screening, wherein the plurality of aptamer particles for each additional round of screening is the enriched aptamer particle pool from the previous round, and each additional round includes exposing the enriched aptamer particle pool to the detectably labeled target, quantitating a signal for each of the particles in the enriched aptamer particle pool, wherein the signal is indicative of a binding interaction between the candidate aptamer sequences bound to each of the aptamer particles and the detectably labeled target, sorting the aptamer particles based on the quantitated signal, and preparing an enriched aptamer particle pool from the isolated subset of the sorted aptamer particles.

As discussed above, the particle-immobilized candidate nucleic acid agents and aptamer particles for each additional round of screening may be the enriched particle pool from the previous round. For example, following a first round of screening in which $1\times10^7$ to $1\times10^8$ particles (i.e., $1\times10^7$ to $1\times10^8$ unique sequences) were screened, an enriched particle pool may be provided which has about $1\times10^7$ to $1\times10^8$ particles, which particles include from about 100 to about 1000 particles with a unique sequence thereon.

In some embodiments, the intensity of the signal which is indicative of a binding interaction between the candidate aptamer sequences bound to each aptamer particle and the detectably labeled target increases with an increase in binding affinity between the candidate aptamer sequences bound to each aptamer particle and the detectably labeled target. Such embodiments may be used to isolate aptamers having high affinity for a particular target in a limited number of rounds. For example, in some embodiments, an aptamer screening method as described herein is capable of identifying aptamer sequences which are capable of binding a specified target with a $K_d$ of from about 1 pM to about 100 nM, e.g., a $K_d$ of from about 1 pM to about 10 nM, or a $K_d$ of from about 1 pM to about 5 nM following a single round of screening. In some embodiments, an aptamer screening method as described herein is capable of identifying aptamer sequences which are capable of binding a specified target with a $K_d$ of from about 1 pM to about 100 nM, e.g., a $K_d$ of from about 1 pM to about 10 nM, or a $K_d$ of from about 1 pM to about 5 nM following one or more rounds of screening, e.g., three rounds of screening.

The enriching steps described above may utilize a nucleic acid amplification method as discussed above, e.g., PCR, reverse transcriptase PCR, or primer extension as appropriate in view of the candidate nucleic acid agent sequences or candidate aptamer sequences being amplified.

Isolation and/or sorting as described herein may be conducted using a variety of methods and/or devices known in the art, e.g., flow cytometry (e.g., Fluorescence Activated Cell Sorting (FACS) or Ramen flow cytometry), fluorescence microscopy, optical tweezers, micro-pipettes, and microfluidic magnetic separation devices and methods. In some embodiments, where the detectably labeled target is a fluorescently labeled target, Fluorescence Activated Cell Sorting (FACS) may be utilized to quantitatively sort particle immobilized candidate nucleic acid agents or aptamer particles based on one or more fluorescence signals. One or more sort gates or threshold levels may be utilized in connection with one or more detectable labels to provide quantitative sorting over a wide range of candidate nucleic acid agent-target interactions or candidate aptamer sequence-target interactions. In addition, the screening stringency may be quantitatively controlled, e.g., by modulating the target concentration and setting the position of the sort gates.

Where, for example, the fluorescence signal is related to the binding affinity of the candidate nucleic acid agents or candidate aptamer sequences for the target, the sort gates and/or stringency conditions may be adjusted to select for nucleic acid agents or aptamers having a desired affinity or desired affinity range for the target. In some cases, it may be desirable to isolate the highest affinity nucleic acid agents or aptamers from a particular library of candidate nucleic acid agents or candidate aptamer sequences. However, in other cases nucleic acid agents or aptamers falling within a particular range of binding affinities may be isolated.

Screening of Candidate Nucleic Acid Agent Conjugates or Candidate Aptamers Conjugates In some embodiments it may be desirable to screen for nucleic acid agents or aptamers which have a desired property, e.g., a desired binding affinity after being linked to another molecule. For example, in some embodiments, it may be of interest to screen for nucleic acid agents or aptamers that have a desired affinity, e.g., the highest affinity, for a particular target after being linked to polyethylene glycol (PEG), a reagent that may confer desirable pharmacokinetic properties when used in vivo. Particle display as described herein can be used to directly screen a candidate nucleic acid agent-PEG conjugate library or a candidate aptamer-PEG conjugate library as opposed to first identifying a nucleic acid agent or aptamer that binds a target and then testing whether affinity is maintained after conjugation with PEG. In some embodiments, following synthesis of particle-immobilized candidate nucleic agents or aptamer particles, PEG-poly T conjugates can be added to the particle-immobilized candidate nucleic acid agent library or aptamer particle library. The particle-immobilized candidate nucleic acid agent sequences or the sequences on the aptamer particles can be ligated to poly T by DNA ligase, and thus effectively ligated to PEG. The particles displaying the candidate nucleic acid agent-PEG conjugates or candidate aptamer-PEG conjugates can then be used for selection using one or more of the methods disclosed herein.

Screening for Structure Switching Activity or Other Desired Properties

Nucleic acid agents or aptamers that significantly change conformation upon target binding can be valuable for sensor design. However, the target binding affinity of the nucleic acid agent or aptamer doesn't necessarily correlate to the structure switching capability. The particle display and screening methods described herein can be used to directly screen for structure switching capability, e.g., instead of binding affinity. For example, in one embodiment, a fluorophore can be incorporated into the candidate nucleic acid agent sequences or candidate aptamer sequences immobilized on the particles. After synthesis of the particle-immobilized candidate nucleic acid agents or aptamer particles, a sequence complementary to the immobilized sequence can be added, which also contains a quencher molecule. The complementary sequence will hybridize with the immobilized sequence by base-pairing, causing the fluorophore to be quenched such that the particles will not fluoresce. Then, a target molecule can be incubated with the particle-immobilized candidate nucleic acid agents or aptamer particles. Those particle-immobilized candidate nucleic acid agents or aptamer particles containing structure switching nucleic acid agents or aptamers will not only bind to the target molecules, but also undergo significant structure switching and displace the quencher-containing complement sequence from the immobilized sequence, resulting in detectable fluorescence. The particle-immobilized candidate nucleic acid agents or aptamer particles that regain fluorescence after the incubation can be collected as candidate structure-switching nucleic acid agents or aptamers.

Other desired properties may be screened for by physically linking an indicator of the desired property, e.g., a target-binding induced activity such as catalytic activity, activation activity, inhibition activity or a cooperative activity, to the candidate nucleic acid agent or candidate aptamer having the desired activity or to those candidate nucleic acid agents or candidate aptamers lacking the desired activity. For example, where the desired activity is the inhibition of a binding reaction between a first target molecule and a second molecule following binding of the first target molecule by the candidate nucleic acid agent or candidate aptamer, a detectable label on the second molecule could be used to distinguish candidate nucleic acid agents or candidate aptamers which have the desired inhibitory activity from those which do not.

Targets

Candidate nucleic acid agents and aptamers may be generated and screened as described herein to identify nucleic acid agents and aptamers which bind to a variety of targets, e.g., target molecules. Suitable targets may include, for example, small molecules (e.g., organic dyes, toxins, etc.), amino acids, carbohydrates, lipids, aminoglycosides, antibiotics, peptides, proteins, post-translational modifications, nucleic acids, liposomes, virus, whole cells, cellular components, tissues, living organisms, or an unknown target or mixture. Small molecule targets of interest generally have a molecular weight of about 1000 Daltons, e.g., less than 800 Daltons. Protein targets of interest may include, for example, cell surface receptors, signal transduction factors, and hormones. Cellular targets of interest may include, for example, mammalian cells, particularly human cells; stem cells; tumor cells and bacterial cells.

More than one type of target may be utilized simultaneously in the screening methods disclosed herein. For example, two or more protein targets having different amino acid sequences may be simultaneously screened against a single library of candidate nucleic acid agents or candidate aptamer sequences.

In some embodiments, a target molecule or a molecule associated with a target molecule, e.g., via a binding interaction, may be detectably labeled as described herein.

Labels

Suitable labels which may be used to provide a detectably labeled target or detectably labeled nucleic acid agent, e.g., aptamer, according to the present disclosure may include radioactive isotopes, fluorescers, chemiluminescers, chromophores, enzymes, enzyme substrates, enzyme cofactors, enzyme inhibitors, dyes, metal ions, metal sols, ligands (e.g., biotin, avidin, strepavidin or haptens), affinity tags and the like.

Exemplary affinity tags suitable for use include, but are not limited to, a monocytic adaptor protein (MONA) binding peptide, a T7 binding peptide, a streptavidin binding peptide, a polyhistidine tract, protein A (Nilsson et al., *EMBO J.* 4:1075 (1985); Nilsson et al., *Methods Enzymol.* 198:3 (1991)), glutathione S transferase (Smith and Johnson, Gene 67:31 (1988)), Glu-Glu affinity tag (Grussenmeyer et al., *Proc. Natl. Acad. Sci.* USA 82:7952 (1985)), substance P, FLAG peptide (Hopp et al., Biotechnology 6:1204 (1988)), or other antigenic epitope or binding domain. See, in general, Ford et al., *Protein Expression and Purification* 2:95 (1991). DNA molecules encoding affinity tags are available from commercial suppliers (e.g., Pharmacia Biotech, Piscataway, N.J.).

Any fluorescent polypeptide (also referred to herein as a fluorescent label) may be suitable for use as a detectable label. A suitable fluorescent polypeptide will be one that will readily provide a detectable signal that can be assessed qualitatively (positive/negative) and quantitatively (comparative degree of fluorescence). Exemplary fluorescent polypeptides include, but are not limited to, yellow fluorescent protein (YFP), cyan fluorescent protein (CFP), GFP, mRFP, RFP (tdimer2), HCRED, etc., or any mutant (e.g., fluorescent proteins modified to provide for enhanced fluorescence or a shifted emission spectrum), analog, or derivative thereof. Further suitable fluorescent polypeptides, as well as specific examples of those listed herein, are provided in the art and are well known.

Biotin-based labels also find use in the methods disclosed herein. Biotinylation of target molecules is well known, for example, a large number of biotinylation agents are known, including amine-reactive and thiol-reactive agents, for the biotinylation of proteins, nucleic acids, carbohydrates, carboxylic acids; see, e.g., chapter 4, Molecular Probes Catalog, Haugland, 6th Ed. 1996, hereby incorporated by reference. A biotinylated substrate can be detected by binding of a detectably labeled biotin binding partner, such as avidin or streptavidin. Similarly, a large number of haptenylation reagents are also known.

Isolated High-Affinity Aptamers

The present disclosure provides isolated high affinity aptamers identified using the methods and compositions disclosed herein.

Aptamers capable of binding to human α-thrombin and including the following DNA sequences are provided in Table 1 below:

TABLE 1

| | |
|---|---|
| Thrombin 01 | AAGTAGGTATGTTTTTTGGGTAGGGTGGTCGAGTTTGCCATTTGCTGCTTGGCGAGCAGC (SEQ ID NO: 1) |
| Thrombin 02 | AAGTAGGTATGTTTTTTGGGTAGGGTGGTCGAGTTTGCCATTTGCTGCTTGGCGAGCAGC (SEQ ID NO: 1) |
| Thrombin 03 | CAGCGCTAGGGCTTTTAGCGTAATGGGTAGGGTGGTGCGGTGCAGATATCGGAATTGGTG (SEQ ID NO: 2) |
| Thrombin 04 | CAGCGCTAGGGCTTTTAGCGTAATGGGTAGGGTGGTGCGGTGCAGATATCGGAATTGGTG (SEQ ID NO: 2) |
| Thrombin 05 | AAGTAGGTATGTTTTTTGGGTAGGGTGGTCGAGTTTGCCATTTGCTGCTTGGCGAGCAGC (SEQ ID NO: 1) |
| Thrombin 06 | TCGGTAGGGTACCTACTGAGGTACATATATGGGTAGGGTGGTCCGGGATTCGTTTTAA (SEQ ID NO: 3) |
| Thrombin 07 | CAGCGCTAGGGCTTTTAGCGTAATGGGTAGGGTGGTGCGGTGCAGATATCGGAATTGGTG (SEQ ID NO: 2) |
| Thrombin 08 | TCGGTAGGGTACCTACTGAGGTACATATATGGGTAGGGTGGTCCGGGATTCGTTTTAA (SEQ ID NO: 3) |
| Thrombin 09 | AAGGCACGAAATGGTTGGGGTGGATGTAGGGGTGCCTCGAGGACCGTTTTTTCTATAAGA (SEQ ID NO: 4) |
| Thrombin 10 | CTAGACGTGCGAAGAGGTACTTATTGTGGTTTGGGTGGTTTCGCTCGCTAGCGATTAGGG (SEQ ID NO: 5) |
| Thrombin 11 | TCGGTAGGGTACCTACTGAGGTACATATATGGGTAGGGTGGTCCGGGATTCGTTTTAA (SEQ ID NO: 3) |
| Thrombin 12 | CAGCGCTAGGGCTTTTAGCGTAATGGGTAGGGTGGTGCGGTGCAGATATCGGAATTGGTG (SEQ ID NO: 2) |
| Thrombin 13 | AAGTAGGTATGTTTTTTGGGTAGGGTGGTCGAGTTTGCCATTTGCTGCTTGGCGAGCAGC (SEQ ID NO: 1) |
| Thrombin 14 | CAGCGCTAGGGCTTTTAGCGTAATGGGTAGGGTGGTGCGGTGCAGATATCGGAATTGGTG (SEQ ID NO: 2) |
| Thrombin 15 | TCGGTAGGGTACCTACTGAGGTACATATATGGGTAGGGTGGTCCGGGATTCGTTTTAA (SEQ ID NO: 3) |
| Thrombin 16 | AAGTAGGTATGTTTTTTGGGTAGGGTGGTCGAGTTTGCCATTTGCTGCTTGGCGAGCAGC (SEQ ID NO: 1) |
| Thrombin 17 | CAGCGCTAGGGCTTTTAGCGTAATGGGTAGGGTGGTGCGGTGCAGATATCGGAATTGGTG (SEQ ID NO: 2) |
| Thrombin 18 | TCGGTAGGGTACCTACTGAGGTACATATATGGGTAGGGTGGTCCGGGATTCGTTTTAA (SEQ ID NO: 3) |
| Thrombin 19 | CAGCGCTAGGGCTTTTAGCGTAATGGGTAGGGTGGTGCGGTGCAGATATCGGAATTGGTG (SEQ ID NO: 2) |
| Thrombin 20 | CAGCGCTAGGGCTTTTAGCGTAATGGGTAGGGTGGTGCGGTGCAGATATCGGAATTGGTG (SEQ ID NO: 2) |

Aptamers capable of binding to recombinant human apolipoprotein E3 (ApoE3) and including the following DNA sequences are provided in Table 2 below:

TABLE 2

| | |
|---|---|
| ApoE 01 | TTGTGGTTGGAGGGGGGTGGGTGGGCGGGCTTTTGCCGATGTCTCTGAGAATCGTAGCAA (SEQ ID NO: 6) |
| ApoE 02 | TTGGGGTTGGTGGGGGCGGGCGGGTGGGTGCGCTTAGACGTGCGTGCGAATTCTGACTG (SEQ ID NO: 7) |
| ApoE 03 | CAGTCCCATTTCTGGGAGGGTTGGATTTACGGGGTGGAGCCCGGAGTGTGGGGTGCGGGG (SEQ ID NO: 8) |
| ApoE 04 | TTGGGGTTGGTGGGGGCGGGCGGGTGGGTGCGCTTAGACGTGCGTGCGAATTCTGACTG (SEQ ID NO: 7) |

TABLE 2 -continued

| | |
|---|---|
| ApoE 05 | CAGTCCCATTTCTGGGAGGGTTGGATTTACGGGGTGGAGCCCGGAGTGTGGGGTGCGGGG (SEQ ID NO: 8) |
| ApoE 06 | GATAAACGCCTTGATTAAAGGCCCAGTTCTTTAGGCCTACACGTGCTGCGACATTAATT (SEQ ID NO: 9) |
| ApoE 07 | TTGGGGTTGGTGGGGGCGGGCGGGTGGGTGCGCTTAGACGTGCGTGCGAATTCTGACTG (SEQ ID NO: 7) |
| ApoE 08 | GATAAACGCCTTGATTAAAGGCCCAGTTCTTTAGGCCTACACGTGCTGCGACATTAATT (SEQ ID NO: 9) |
| ApoE 09 | TTGTGGTTGGAGGGGGGTGGGTGGGCGGGCTTTTGCCGATGTCTCTGAGAATCGTAGCAA (SEQ ID NO: 6) |
| ApoE 10 | CAGTCCCATTTCTGGGAGGGTTGGATTTACGGGGTGGAGCCCGGAGTGTGGGGTGCGGGG (SEQ ID NO: 8) |
| ApoE 11 | CAGTCCCATTTCTGGGAGGGTTGGATTTACGGGGTGGAGCCCGGAGTGTGGGGTGCGGGG (SEQ ID NO: 8) |
| ApoE 12 | GATAAACGCCTTGATTAAAGGCCCAGTTCTTTAGGCCTACACGTGCTGCGACATTAATT (SEQ ID NO: 9) |
| ApoE 13 | CAGTCCCATTTCTGGGAGGGTTGGATTTACGGGGTGGAGCCCGGAGTGTGGGGTGCGGGG (SEQ ID NO: 8) |
| ApoE 14 | TTGGGGTTGGTGGGGGCGGGCGGGTGGGTGCGCTTAGACGTGCGTGCGAATTCTGACTG (SEQ ID NO: 7) |
| ApoE 15 | CAGTCCCATTTCTGGGAGGGTTGGATTTACGGGGTGGAGCCCGGAGTGTGGGGTGCGGGG (SEQ ID NO: 8) |
| ApoE 16 | GATAAACGCCTTGATTAAAGGCCCAGTTCTTTAGGCCTACACGTGCTGCGACATTAATT (SEQ ID NO: 9) |
| ApoE 17 | TTGGGGTTGGTGGGGGCGGGCGGGTGGGTGCGCTTAGACGTGCGTGCGAATTCTGACTG (SEQ ID NO: 7) |
| ApoE 18 | GATAAACGCCTTGATTAAAGGCCCAGTTCTTTAGGCCTACACGTGCTGCGACATTAATT (SEQ ID NO: 9) |
| ApoE 19 | GATAAACGCCTTGATTAAAGGCCCAGTTCTTTAGGCCTACACGTGCTGCGACATTAATT (SEQ ID NO: 9) |
| ApoE 20 | TTGGGGTTGGTGGGGGCGGGCGGGTGGGTGCGCTTAGACGTGCGTGCGAATTCTGACTG (SEQ ID NO: 7) |

Aptamers capable of binding to human plasminogen activator inhibitor 1 (PAI-1) and including the following DNA sequences are provided in Table 3 below:

TABLE 3

| | |
|---|---|
| PAI-1 01 | CATTGAGATAGCTAGTTGTAGCTGCGTCATAGGCTGGGTTGGGTCTAGTGGTTGGGTGTG (SEQ ID NO: 10) |
| PAI-1 02 | CATTGAGATAGCTAGTTGTAGCTGCGTCATAGGCTGGGTTGGGTCTAGTGGTTGGGTGTG (SEQ ID NO: 10) |
| PAI-1 03 | CACTTCGATTGTCGTGGAGGTGGGGGTGGGTGTGGGTGGGGTGAGACCGTGCATCGGCCG (SEQ ID NO: 11) |
| PAI-1 04 | CGGGGACACGGGGTGGACGAAGTGGGTTGTGTGTGGATGGGAGGGGCATGTCACCCCTGG (SEQ ID NO: 12) |
| PAI-1 05 | CGGGGACACGGGGTGGACGAAGTGGGTTGTGTGTGGATGGGAGGGGCATGTCACCCCTGG (SEQ ID NO: 12) |
| PAI-1 06 | GACATGGTGGGTGTGTGGGGGTGGGCGGAGGGTTGGTGGTCCGCTGGCCTTAGAAGGCGC (SEQ ID NO: 13) |
| PAI-1 07 | CATTGAGATAGCTAGTTGTAGCTGCGTCATAGGCTGGGTTGGGTCTAGTGGTTGGGTGTG (SEQ ID NO: 10) |

TABLE 3 -continued

| | |
|---|---|
| PAI-1 08 | CGGGGACACGGGGTGGACGAAGTGGGTTGTGTGTGGATGGGAGGGGCATGTCACCCCTGG (SEQ ID NO: 12) |
| PAI-1 09 | CGGGGACACGGGGTGGACGAAGTGGGTTGTGTGTGGATGGGAGGGGCATGTCACCCCTGG (SEQ ID NO: 12) |
| PAI-1 10 | CATTGAGATAGCTAGTTGTAGCTGCGTCATAGGCTGGGTTGGGTCTAGTGGTTGGGTGTG (SEQ ID NO: 10) |
| PAI-1 11 | CATTGAGATAGCTAGTTGTAGCTGCGTCATAGGCTGGGTTGGGTCTAGTGGTTGGGTGTG (SEQ ID NO: 10) |
| PAI-1 12 | CATTGAGATAGCTAGTTGTAGCTGCGTCATAGGCTGGGTTGGGTCTAGTGGTTGGGTGTG (SEQ ID NO: 10) |
| PAI-1 13 | CGGGGACACGGGGTGGACGAAGTGGGTTGTGTGTGGATGGGAGGGGCATGTCACCCCTGG (SEQ ID NO: 12) |
| PAI-1 14 | CATTGAGATAGCTAGTTGTAGCTGCGTCATAGGCTGGGTTGGGTCTAGTGGTTGGGTGTG (SEQ ID NO: 10) |
| PAI-1 15 | CGGGGACACGGGGTGGACGAAGTGGGTTGTGTGTGGATGGGAGGGGCATGTCACCCCTGG (SEQ ID NO: 12) |
| PAI-1 16 | CGGGGACACGGGGTGGACGAAGTGGGTTGTGTGTGGATGGGAGGGGCATGTCACCCCTGG (SEQ ID NO: 12) |
| PAI-1 17 | CATTGAGATAGCTAGTTGTAGCTGCGTCATAGGCTGGGTTGGGTCTAGTGGTTGGGTGTG (SEQ ID NO: 10) |
| PAI-1 18 | CATTGAGATAGCTAGTTGTAGCTGCGTCATAGGCTGGGTTGGGTCTAGTGGTTGGGTGTG (SEQ ID NO: 10) |
| PAI-1 19 | CATTGAGATAGCTAGTTGTAGCTGCGTCATAGGCTGGGTTGGGTCTAGTGGTTGGGTGTG (SEQ ID NO: 10) |
| PAI-1 20 | CACTTCGATTGTCGTGGAGGTGGGGGTGGGTGTGGGTGGGGTGAGACCGTGCATCGGCCG (SEQ ID NO: 11) |

Aptamers capable of binding to recombinant human 4-1BB/TNFRSF9/CD137 Fc Chimera and including the following DNA sequences are provided in Table 4 below:

TABLE 4

| | |
|---|---|
| 4-1BB 01 | ATCCACGAAGTAGACTGTCTAGGTTGGGTAGGGTGGTGACAGTGTCTGGGAAGGCTGCGC (SEQ ID NO: 14) |
| 4-1BB 02 | ATCCACGAAGTAGACTGTCTAGGTTGGGTAGGGTGGTGACAGTGTCTGGGAAGGCTGCGC (SEQ ID NO: 14) |
| 4-1BB 03 | GGCGGTCGTAATGTGGTTGTGGTTGGTGGGGGCGGGTGGGTTGGGAGAGGACGAGGCGC (SEQ ID NO: 15) |
| 4-1BB 04 | GTCAGATTCCACTATAGTAGGTTGGGTATGGTGGTCGCAGTGGATGATATGTCGTAGGGG (SEQ ID NO: 16) |
| 4-1BB 05 | ATGTCGAGTAGGTTGGGTAGGGTGGTCGTTGATATCATTTATATTCCCTGCTAGTCTGC (SEQ ID NO: 17) |
| 4-1BB 06 | ATCCACGAAGTAGACTGTCTAGGTTGGGTAGGGTGGTGACAGTGTCTGGGAAGGCTGCGC (SEQ ID NO: 14) |
| 4-1BB 07 | GTCAGATTCCACTATAGTAGGTTGGGTAGGGTGGTCGCAGTGGATGATATGTCGTAGGGG (SEQ ID NO: 18) |
| 4-1BB 08 | GTCAGATTCCACTATAGTAGGTTGGGTAGGGTGGTCGCAGTGGATGATATGTCGTAGGGG (SEQ ID NO: 18) |
| 4-1BB 09 | GTCAGATTCCACTATAGTAGGTTGGGTAGGGTGGTCGCAGTGGATGATATGTCGTAGGGG (SEQ ID NO: 18) |
| 4-1BB 10 | ATCCACGAAGTAGACTGTCTAGGTTGGGTAGGGTGGTGACAGTGTCTGGGAAGGCTGCGC (SEQ ID NO: 14) |

TABLE 4 -continued

```
4-1BB 11   GTCAGATTCCACTATAGTAGGTTGGGTAGGGTGGTCGCAGTGGATGATATGTCGTAGGGG
           (SEQ ID NO: 18)

4-1BB 12   ATCCACGAAGTAGACTGTCTAGGTTGGGTAGGGTGGTGACAGTGTCTGGGAAGGCTGCGC
           (SEQ ID NO: 14)

4-1BB 13   GGCGGTCGTAATGTGGTTGTGGTTGGTGGGGGCGGGTGGGTTGGGAGAGGACGAGGCGC
           (SEQ ID NO: 15)

4-1BB 14   ATCCACGAAGTAGACTGTCTAGGTTGGGTAGGGTGGTGACAGTGTCTGGGAAGGCTGCGC
           (SEQ ID NO: 14)

4-1BB 15   ATCCACGAAGTAGACTGTCTAGGTTGGGTAGGGTGGTGACAGTGTCTGGGAAGGCTGCGC
           (SEQ ID NO: 14)

4-1BB 16   GTCAGATTCCACTATAGTAGGTTGGGTATGGTGGTCGCAGTGGATGATATGTCGTAGGGG
           (SEQ ID NO: 16)

4-1BB 17   GTCAGATTCCACTATAGTAGGTTGGGTAGGGTGGTCGCAGTGGATGATATGTCGTAGGGG
           (SEQ ID NO: 18)

4-1BB 18   GTCAGATTCCACTATAGTAGGTTGGGTAGGGTGGTCGCAGTGGATGATATGTCGTAGGGG
           (SEQ ID NO: 18)

4-1BB 19   GTCAGATTCCACTATAGTAGGTTGGGTAGGGTGGTCGCAGTGGATGATATGTCGTAGGGG
           (SEQ ID NO: 18)

4-1BB 20   GTCAGATTCCACTATAGTAGGTTGGGTAGGGTGGTCGCAGTGGATGATATGTCGTAGGGG
           (SEQ ID NO: 18)
```

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Aptamer Particle (Ap) Synthesis

1. Methods and Materials

Coupling Forward Primers (FP) to Particles:

As a first step in the preparation of APs, forward primers (FP) were coupled to magnetic particles using the following methods.

500 µL of 1-µm MyOne carboxylic acid magnetic particles ($10^7$/µL, Life Technologies) were washed once with 500 µL of 0.01N NaOH, and then three times with 1 mL of nuclease-free water. After the last wash, the particles were resuspended in a 150 µL reaction mixture containing 200 mM NaCl, 0.2 mM 5'-amino-modified FP (5'-amino-PEG18-AGC AGC ACA GAG GTC AGA TG-3') (SEQ ID NO:19), 1 mM imidazole chloride, 50% v/v dimethyl sulfoxide (DMSO) and 250 mM 1-ethyl-3-(3-dimethylaminopropyl) carbodiimide (EDC). Amino group modification was chosen because this coupling is covalent and can keep FPs attached to the particles during thermal cycling, with the PEG18 at the 5' end of FP serving as a spacer. Particles were mixed well with reagents, vortexed, sonicated and incubated overnight at room temperature on a rotator. In order to reduce non-specific interaction between the particles and target molecules, remaining carboxyls on the particles were converted into amino-reactive NHS-ester in the presence of 250 mM EDC and 100 mM N-hydroxysuccinimide (NHS) in 2-(N-morpholino)ethanesulfonic acid (MES) buffer (100 mM, PH 4.7) for 30 minutes at room temperature, followed by conjugation with 20 mM amino-PEG12 (Pierce) in IVIES buffer for one hour. The particles were then washed four times with 500 µL of TE buffer (10 mM Tris, pH 8.0, 0.1 mM EDTA), and finally suspended in 500 µL of TE buffer and stored at 4° C.

To test the conjugation efficiency, 1 µM Alexa Fluor 647-modified FP complementary sequence (FPC) was incubated with 0.2 µL of FP particles in 100 µL of STE buffer (10 mM Tris pH 8.0, 50 mM NaCl, 1 mM EDTA) at 59° C. for 10 minutes, then snap cooled on ice for 2 minutes. The particles were then washed twice with 100 µL STE buffer and analyzed by Accuri C6 Flow Cytometer (BD Biosciences).

Aptamer Particle (AP) Synthesis:

Following the coupling of FP to particles, aptamer particles (AP) were synthesized as indicated below.

In vitro display of aptamers on synthetic particles was achieved via emulsion PCR (see, e.g., Dressman et al. (2003) *Proceedings of the National Academy of Sciences of the United States of America* 100:8817-22; Diehl, F. et al. (2006) *Nature methods* 3: 551-9). The oil phase was composed of 4.5% Span 80, 0.40% Tween 80 and 0.05% Triton X-100 in mineral oil, all of which were purchased from Sigma-Aldrich. This oil phase was freshly prepared each day. The aqueous phase consisted of 1×PCR buffer, 25 mM $MgCl_2$, 3.5 mM of each dNTP, 40 nM FP, 3 µM reverse primer (RP), 0.25 U/µL of GoTaq Hot Start Polymerase (Promega), 1 pM template DNA, and 3×10⁸ FP-coated particles in a total volume of 1 mL. Water-in-oil emulsions were prepared by drop-wise addition of 1 mL of the aqueous phase to 7 mL of the oil phase, which was previously placed in a DT-20 tube (IKA) locked into the Ultra-Turrax Device (IKA). This drop-wise addition was performed over 30 seconds while the mixture was being stirred at 620 rpm in the Ultra-Turrax. After addition of the aqueous phase, stirring of the mixture was continued for a total of 5 min. The emulsions were distributed in 100 µL aliquots into ~80 wells of a 96-well PCR plate. PCR was carried out under the following cycling conditions: 95° C. for 3 min, followed by 40 cycles of 93° C. for 15 sec, 59° C. for 30 sec and 72° C. for 75 sec. After PCR, the emulsions were collected into an emulsion collection tray (Life Technologies) by centrifuging at 500 rpm for 2 minutes. Next, the emulsion was broken by adding 10 mL 2-butanol to the emulsion collection tray, and transferring the collected sample to a 50 mL tube. After vortexing for 30 sec, the particles were pelleted by centrifugation at 5,000×g for 5 minutes. After carefully removing the top oil phase, the particles were resuspended in 600 µL of emulsion breaking (EB) buffer (100 mM NaCl, 1% Triton X-100, 10 mM Tris-HCl, pH 7.5, and 1 mM EDTA) and were transferred to a new 1.5 mL tube. After vortexing for 30 sec and centrifugation for 90 sec at 15,000×g, the supernatant was removed. The tube was then placed on a magnetic separator (MPC-S, Life Technologies), and the rest of the supernatant was pipetted off carefully. The particles were washed an additional three times with TE buffer by using magnetic separation, and then finally resuspended in 3000 µL TE buffer.

To generate single-stranded DNA, the tube was placed on the magnet to concentrate the particles for 1 min, and the supernatant was carefully removed with a pipette tip. The particles were then resuspended in 200 µM of 0.1 M NaOH and incubated for 2 min. The tube was placed in the magnetic separator for 1 min and the supernatant was carefully removed. This removed the non-biotinylated DNA strand from the particles. After repeating this step twice, the particles were resuspended in 300 µL of TE buffer.

The particles were then annealed with Alexa Fluor 647-labeled RP in STE buffer at 59° C. for 10 minutes and snap-cooled on ice for 2 minutes. The particles were then washed twice with 100 µL STE buffer and analyzed by flow cytometry (FIG. 4, panel (a), panel (c)).

qPCR was performed with an iQ5 instrument (Bio-Rad) to estimate the copy number of aptamers on each AP. The calibration samples were prepared by adding 10⁶, 10⁷, 10⁸, 10⁹ or 10¹⁰ templates into a 20 µL reaction containing 250 nM each of FP and RP, 1,000 FP-coated particles, 10 µL GoTaq PCR Master Mix (Promega), and 0.5×SYBR green. Test samples were prepared identically, but with 1,000 aptamer particles (APs).

Figure 4:
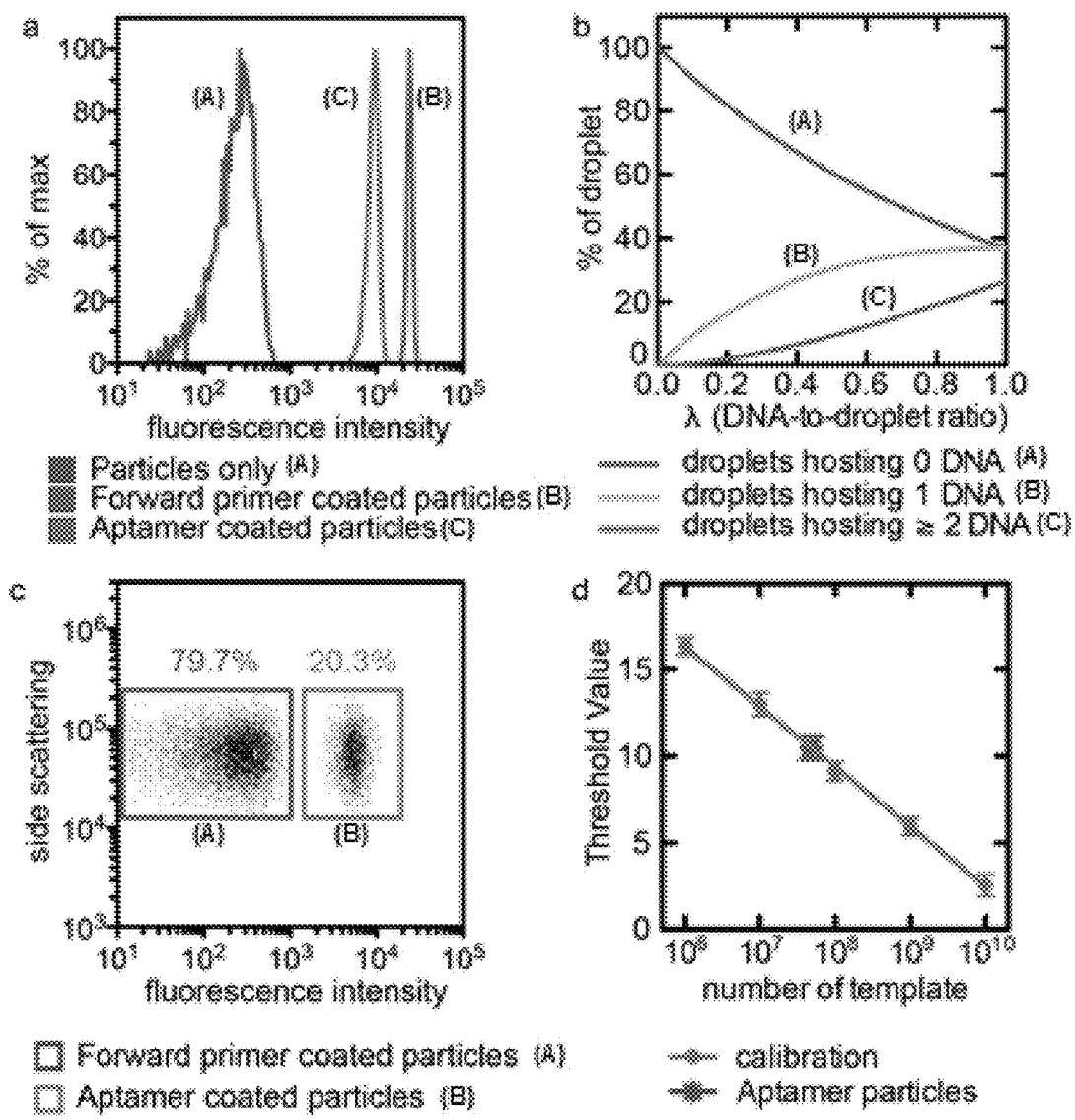
FIG. 4: Validation of the particle display aptamer screening system. (Panel (a)) Typical FACS histogram of singlet particles (Identifier (A)), FP-coated singlet particles hybridized with an Alexa Fluor488-labeled FP complementary probe (Identifier (B)), and ssDNA-displaying singlet particles hybridized with Alexa Fluor488-labeled RP after particle PCR (Identifier (C)). FPs were successfully conjugated to the particles, and ~37.2% of the particle-bound FPs yielded PCR amplification products. (Panel (b)) Effect of total template DNA number on the range of template copies per droplet, assuming Poisson distribution. When template DNA number is equal to the number of droplets, roughly 37% of droplets host no template DNA at all, whereas approximately 26% of droplets host two or more different templates. Since no more than one template molecule should be present per droplet, total template DNA copy number should be kept below 30%—and ideally at 20%—of the total droplet number to minimize chimera formation. (Panel (c)) A typical FACS dot plot of singlet particles after emulsion PCR and annealing with Alexa Fluor 488-labeled RP. 20.3% of the particles contained PCR products, indicating that most particles were clonal according to Poisson distribution. (Panel (d)) qPCR was performed to quantify aptamer copy number for each AP. Threshold cycle values are plotted as a function of template number.

2. Results:

From the threshold cycle, it was calculated that there were 4.8×10⁷ sequences on 1,000 APs (FIG. 4, panel (d)). Since only 20% of APs display template sequences, the average copy number of sequences on each template bearing AP is around 2.4×10⁵.

Example 2: Optimization of Aptamer Particle (Ap) Synthesis

1. Methods and Materials

As discussed above, APs may be formed by performing PCR on the surfaces of magnetic beads within water-in-oil emulsions where each droplet ideally contains a single FP-coated magnetic particle and a single template DNA molecule. (FIG. 2, panel (a), step 1, FIG. 4, panel (a)). The efficiency of the process for generating ssDNA-conjugated particles was first tested. It was determined that 5' amino-modified FP can be covalently conjugated to 1-µm-diameter carboxylic acid particles and remain stable during PCR thermal cycling. After the particles were coupled with FP, particle PCR was performed using the FP-coated particles to display an individual test sequence on the particles. The reverse strands were removed by adding NaOH after completing 30 cycles of PCR. To test the FP conjugation and particle PCR efficiency, aliquots of these particles were annealed with Alexa Fluor 488-labeled FPC or RP and their fluorescence intensity was measured using FACS. Mean fluorescence measurements of 24,564 (FPC) and 9,141 (RP) (FIG. 4, panel (a)) were obtained, respectively correlating with the number of FP and amplified sequences bound to the particle surface. This showed that ~37.2% of particle-coupled FPs were extended during the PCR, with amplification efficiency potentially limited by steric hindrance at the particle surface.

The allocation patterns of template DNA and FP-coated particles roughly follows a Poisson distribution. The probability that there are exactly k DNA molecules or k FP-coated particles in one droplet is therefore equal to:

$$f(k;\lambda) = \frac{\lambda^k e^{-\lambda}}{k!},\quad \text{Eq. 5}$$

where λ is the input DNA:droplet or particle:droplet ratio. Taking the template distribution as an example, the amount of DNA template used in the emulsion PCR is an important parameter affecting this outcome. Using too little template results in too few positive particles, compromising the diversity of the particle population, while too much template results in too many droplets containing multiple templates, causing particles to display combinations of sequences on their surfaces (FIG. 4, panel (b)). Based on the Poisson distribution, one can be sure that most particles are clonal when 20±15% of the particles contain PCR products. After performing emulsion PCR within the droplets such that multiple copies of a single clonal aptamer are immobilized on each particle surface (FIG. 2, panel (a), step 2), the emulsions were broken and the reverse strand of DNA was removed. The AP synthesis outcome was then tested using FACS after the APs were annealed with fluorescently labeled reverse primers (RPs) (FIG. 4, panel (c)).

2. Results

The FACS results confirmed that the APs were clonal because 20±15% of APs typically displayed aptamers on their surface. It was further determined that each AP displayed ~2.4×10⁵ copies of one unique aptamer on its surface using qPCR (FIG. 4, panel (d)). Overall, from a 1 mL PCR reaction, 10⁸ APs were generated, a one-to-one representation of 10⁸ unique DNA sequences.

Example 3: De Novo Particle Display Aptamer Screen Against Four Protein Targets

1. Methods and Materials

Biotinylation of Protein Targets:

Exemplary protein targets for use in validating the theoretical advantages of the systems and methods disclosed herein were prepared as follows. The following (His)₆ tag-labeled protein targets were purchased: human alphathrombin (Haematologic Technologies, Inc., Catalog #: HCT-0020), recombinant human Apolipoprotein E3 (ApoE3) (R&D Systems, Accession #:P02649), Recombinant Human 4-1BB/TNFRSF9/CD137 Fc Chimera (R&D Systems, Accession #:Q07011) and Human Plasminogen activator inhibitor-1 (PAI-1) (Millipore, UniProt Number: P05121). All four proteins were biotinylated using the EZ-Link Micro NHS-PEO$_4$-Biotinylation Kit (Pierce Biotechnology), which includes a polyethylene glycol (PEG) spacer to improve the water solubility of the biotinylated protein. The concentrations of all four proteins were adjusted to 0.5 mg/mL using phosphate-buffered saline (PBS) prior to biotinylation. 50-fold molar excess of biotin reagent was typically used to label 50-100 μg protein for 30 minutes at room temperature. Free biotin was then removed using the Zeba Desalt Spin Column (0.5 mL, Pierce Biotechnology). The final concentration of the biotinylated proteins was determined based on absorbance at 280 nm using a NanoDrop spectrophotometer.

Particle Display Screening:

During each round of screening, ~$10^8$ aptamer particles (APs) were incubated in 2 mL of PBSMCT (DPBS with 2.5 mM MgCl$_2$, 1 mM CaCl$_2$, 0.05% TWEEN-20) with biotinylated proteins, and then washed and incubated with 50 nM streptavidin-phycoerythrin (PE) conjugate (Life Technologies). The exact target concentrations used for each protein are listed in Table 5 below. Labeling with streptavidin-PE allowed isolation by flow cytometric sorting of those APs retaining the highest levels of fluorescence. The target concentrations and gate settings were determined experimentally based on the theoretical analysis discussed in greater detail below. Specifically, during the experiments, the sort gate was set at $F_{max}/3$ and the fluorescence distribution of APs was monitored at a range of different target concentrations, and the target concentration at which ~0.1% of the APs resided in the sort gate was chosen. Once the target concentration was determined, the reaction volume was chosen such that target binding to particle-displayed aptamers would not be under depleting conditions, meaning most target molecules remained unbound from aptamers and free in solution after the reaction reached equilibrium. After collecting the highest-fluorescence APs by FACS, PCR was performed using the DNA on their surfaces as template to generate an enriched pool of aptamers for a subsequent round of AP synthesis. Three rounds of FACS screening and AP amplification were performed for each target. After three rounds of screening, the average $k_d$ of the R3 pool was estimated by measuring the mean fluorescence of all APs outside of the reference gate under a range of different [T], and the [T] at which the mean fluorescence of this population was equal to $(F_{max}+F_{bg})/2$, which represents the average $k_d$ of the pool was determined.

De Novo Particle Display Aptamer Screen Against Four Protein Targets:

In order to experimentally validate the clear theoretical advantage of the system disclosed herein in isolating high-affinity aptamers, particle display screens were performed against four target proteins—thrombin, ApoE, PAI-1 and 4-1 BB—using the optimal conditions identified in the theoretical analysis. It is possible to begin the particle display screen with a large random library, but due to the practical limits of FACS throughput (~$10^7$ particles per hour), one round of magnetic bead-based enrichment was first performed with a random library of ~$10^{14}$ single-stranded DNA molecules and this enriched pool was used to synthesize the initial AP library. Prior to the screen, FACS was performed with APs displaying only the forward primer (FP) to define the reference gate (FIG. 5, panel (a)). APs residing in this reference gate exhibited negligible binding to target proteins, and were not collected during the screen.

Figure 5:
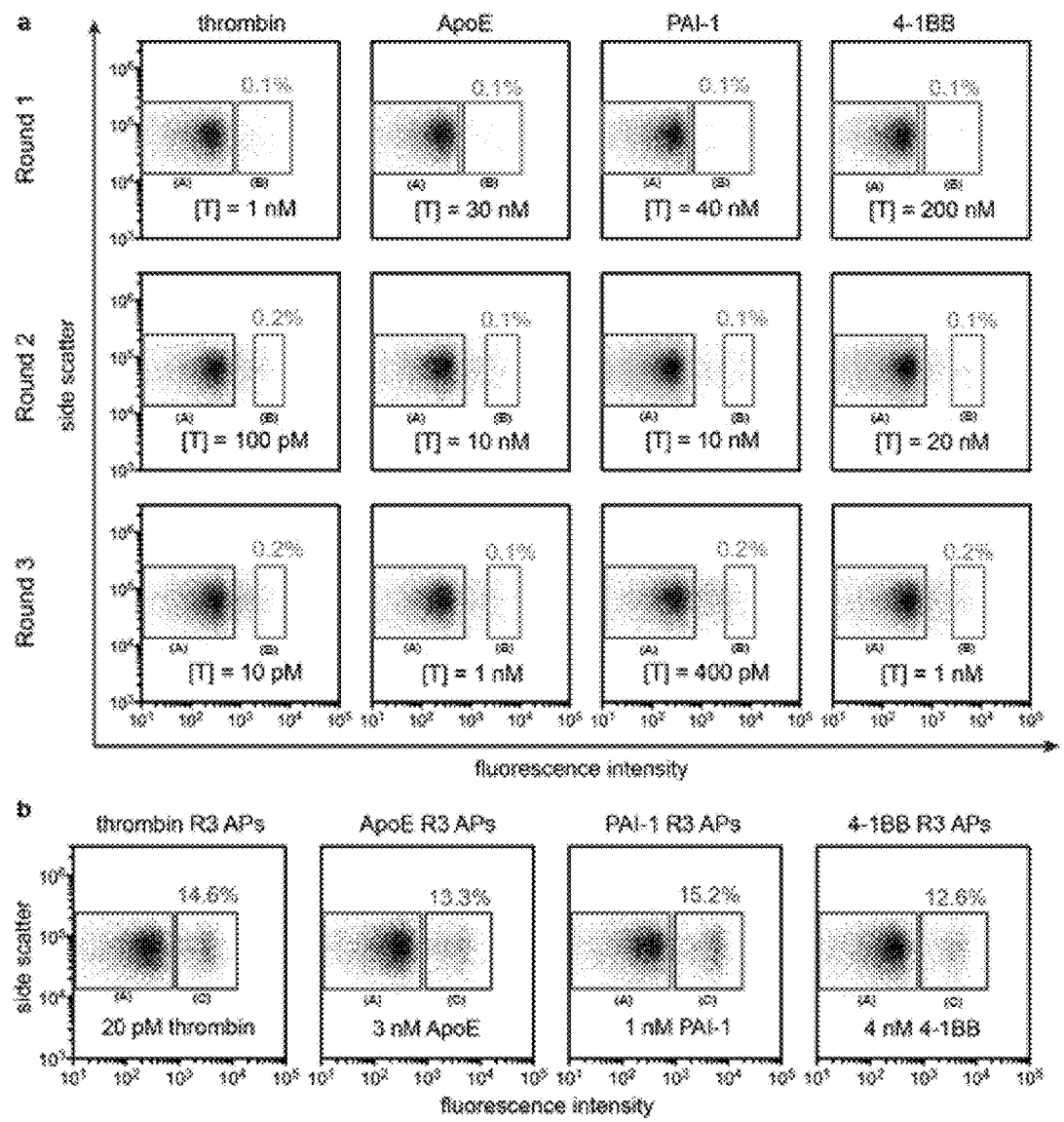
FIG. 5: Particle display screening progress and outcome. (Panel (a)) FACS plots with sort gates for three screening rounds with four different protein targets. [T] is shown for each round, and each dot represents an individual AP. APs residing within reference gates (A) displayed FP or non-binding aptamers, while APs residing within the sort gate (B) displayed aptamers with desired affinity. Collected APs from the sort gate were used as templates for the subsequent round. (Panel (b)) Aptamers isolated in R3 exhibited high target affinities. The average $k_d$ of the R3 pools were 20 pM (thrombin), 3 nM (ApoE), 1 nM (PAI-1) and 4 nM (4-1BB), as measured by the mean fluorescence of the APs outside of the reference gate (C).

Three rounds (R1-3) of particle display screen were performed for all four targets, and FACS plots are shown in FIG. 5, panel (a). Experimental conditions used in all rounds are summarized in Table 5. Due to the limited initial copy number of each AP, it may be important to avoid loss of potentially high-affinity APs in R1; thus, lower screening stringency was applied by setting the sort gate (Identifier B) close to the reference gate (Identifier A), or with some overlap, such that at least 0.1% of the APs were collected (FIG. 5, panel (a), row 1). Aptamers isolated in R1 were PCR amplified and used to synthesize a new set of APs; in this way, 1000 copies of each AP isolated from R1 were available for R2. In R2 and R3, the theoretical optimal screening stringency was used, setting the sort gate at $F_{max}/3$ and decreasing [T] such that ~0.1-0.2% of the Aps was collected (FIG. 5, panel (a), rows 2 and 3). Comparing R3 APs to the starting pool of pre-enriched APs, it was observed that a larger fraction of the AP population resided outside of the reference gate at lower [T]. For example, in the case of thrombin, 0.1% of pre-enriched APs was measured (FIG. 5, panel (a)) versus 14.6% of R3 APs (FIG. 5, panel (b)) at a 50-fold lower thrombin concentration, indicating significant enrichment of high-affinity aptamers.

2. Results

Aptamers isolated in R3 exhibited high affinities for their targets. To estimate average $k_d$, all APs outside of the reference gate (FIG. 5, panel (b), (Identifier C)) were measured, and the [T] at which the mean fluorescence of this population is $(F_{max}+F_{bg})/2$ (see above methods and materials) was measured. The average $k_d$ was found to be 20 pM, 3 nM, 1 nM and 4 nM for thrombin, ApoE, PAI-1 and 4-1BB, respectively.

TABLE 5

Experimental conditions for particle display.

| Target | [T] | # of AP sorted | # of AP collected | [T] | # of AP sorted | # of AP collected | [T] | # of AP sorted | # of AP collected |
|---|---|---|---|---|---|---|---|---|---|
| Thrombin | 1 nM | $10^8$ | $1.1 \times 10^5$ | 100 pM | $10^7$ | $1.5 \times 10^4$ | 10 pM | $6 \times 10^6$ | $1.0 \times 10^4$ |
| ApoE | 30 nM | $10^8$ | $1.3 \times 10^5$ | 10 nM | $10^7$ | $1.0 \times 10^4$ | 1 nM | $9 \times 10^6$ | $1.3 \times 10^4$ |
| PAI-1 | 40 nM | $10^8$ | $1.2 \times 10^5$ | 10 nM | $10^7$ | $9.4 \times 10^3$ | 400 pM | $8 \times 10^6$ | $1.4 \times 10^4$ |
| 4-1BB | 200 nM | $10^8$ | $1.4 \times 10^5$ | 20 nM | $10^7$ | $1.3 \times 10^4$ | 1 nM | $5 \times 10^6$ | $9.2 \times 10^3$ |
| | particle display Round 1 | | | particle display Round 2 | | | particle display Round 3 | | |

Example 4: Characterization of High-Affinity Aptamers

1. Methods and Materials

Figure 6:
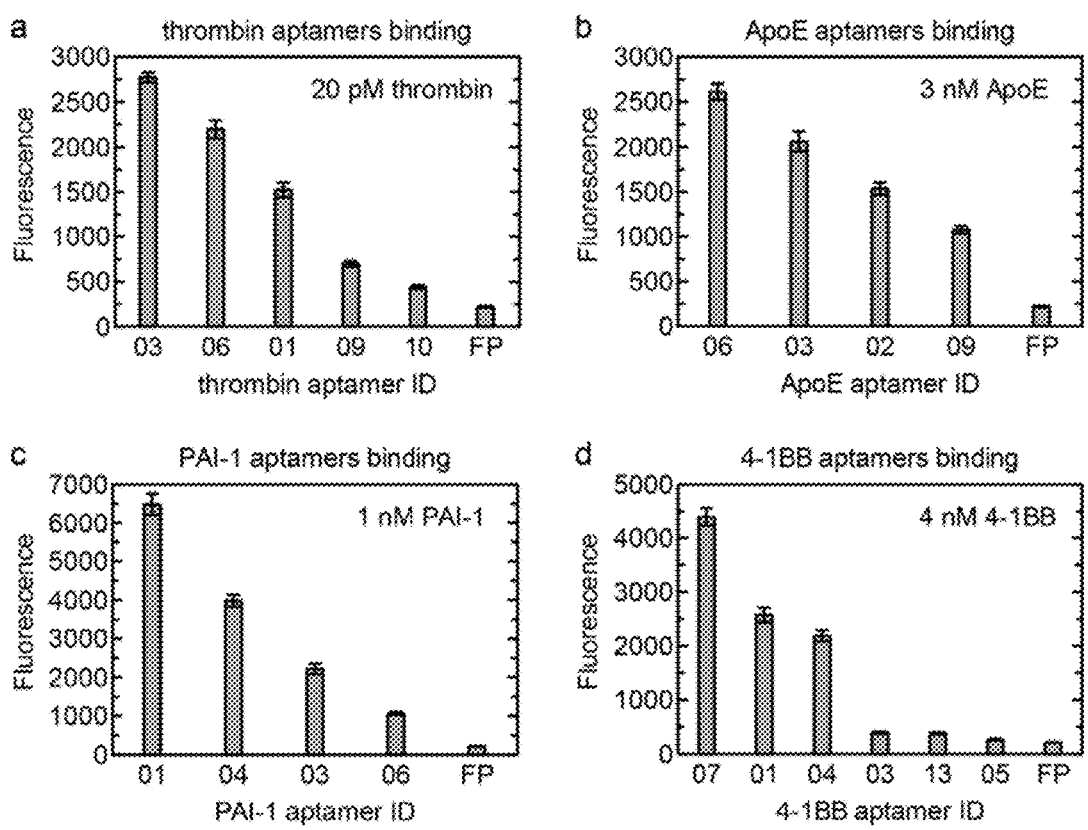
FIG. 6: Aptamer target binding. The relative binding affinities of selected aptamer candidates were quantified from each screening using a bead-based fluorescence binding assay. Different APs, each displaying a unique aptamer sequence, were incubated with target at a single concentration. FP indicates a non-binding forward primer-displaying particle included as a negative control in each measurement. The best candidate aptamer was chosen for each target for further analysis and determination of equilibrium dissociation binding constant ($k_d$). (Panel (a)) thrombin aptamers with [thrombin]=20 pM. (Panel (b)) ApoE aptamers with [ApoE]=3 nM. (Panel (c)) PAI-1 aptamers with [PAI-1]=1 nM. (Panel (d)) 4-1BB aptamers with [4-1BB]=4 nM.

High-affinity aptamers resulting from the above aptamer screen were characterized according to the following methods. To obtain individual aptamer sequences, the R3 pools were cloned into competent bacterial cells and 20 clones from each were randomly picked and sequenced. Clone sequences are shown in FIG. 9, depicting and Tables 1-4. Particle PCR was then performed to synthesize a set of APs displaying each unique sequence (FIG. 4, panel (a)), and their relative binding at a fixed target concentration was measured. The aptamers were rank-ordered based on these affinity data in order to rapidly identify the best candidate for each target (FIG. 6), and then the $k_d$ for these sequences was determined using a fluorescence binding assay.

2. Results

Figure 7:
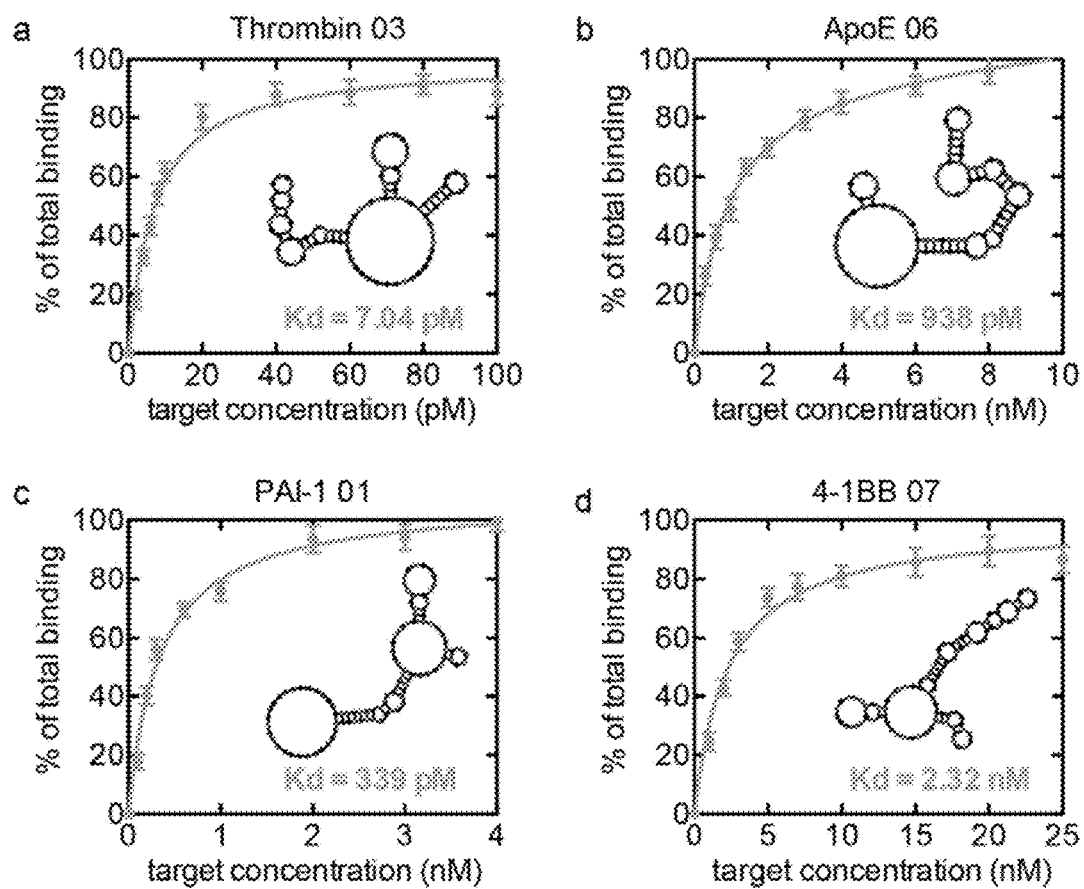
FIG. 7: Affinity measurements of individual aptamers. A bead-based fluorescence assay was used to measure the binding affinity of the top aptamers against (Panel (a)) thrombin, (Panel (b)) ApoE, (Panel (c)) PAI-1 and (Panel (d)) 4-1BB. $k_d$ was calculated using a Langmuir 1:1 binding model and aptamer secondary structure was predicted using mfold (M. Zuker. Mfold web server for nucleic acid folding and hybridization prediction. *Nucleic Acids Res.* 31 (13), 3406-3415, 2003).
Figure 8:
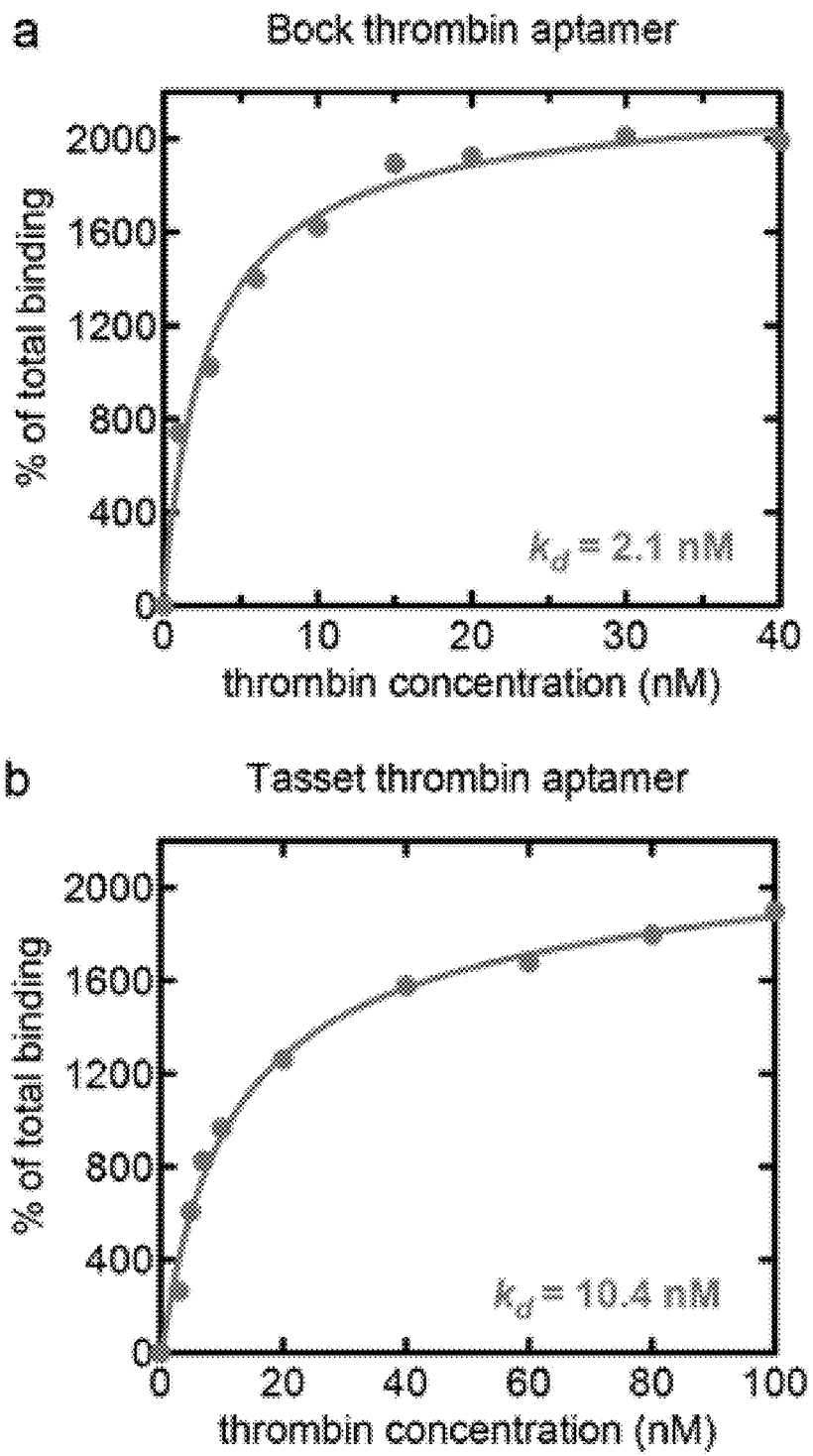
FIG. 8: Affinity of previously published aptamers to thrombin. Bead-based fluorescence binding data for previously published (a) Bock and (b) Tasset thrombin aptamers showing measured $k_d$ of 2.1 nM and 10.4 nM, respectively.

All of the tested sequences exhibited high affinities for their target (Table 3). Their binding curve and secondary structures as predicted by mfold (Zuker, M. Mfold web server for nucleic acid folding and hybridization prediction. *Nucleic acids research* 31, 3406-15 (2003)) are presented in FIG. 7. The affinities of the aptamers against thrombin and ApoE were found to be significantly higher than any previously reported aptamers. For example, thrombin aptamer Thrombin 03 exhibited a $k_d$ of 7.04 pM (FIG. 7, panel (a)), which surpasses the values obtained with the same binding assay using aptamers previously reported by Bock (Bock et al. (1992) Nature 355:564-6) and Tasset (Tasset et al. (1997) *Journal of molecular biology* 272, 688-98) by approximately two to three orders of magnitude (FIG. 8). Similarly, the ApoE aptamer ApoE-06 exhibited a $k_d$ of 938 pM (FIG. 7, panel (b)), a 4-fold improvement over the aptamer recently isolated using high-stringency microfluidic SELEX (Ahmad, K. M. et al. (2011) *PloS one* 6, e27051). Importantly, previously reported selections against PAI-1 and 4-1BB have repeatedly failed without the use of modified bases (Vaught et al. (2010) *Journal of the American Chemical Society* 132:4141-51; Gold et al. (2010) *PloS one* 5, e15004). However, using the disclosed methods, high affinity aptamers were successfully generated for these proteins based entirely on natural DNA; the PAI-1-01 sequence exhibited a $k_d$ of 339 pM (FIG. 6c) and 4-1BB-07 showed a $k_d$ of 2.32 nM (FIG. 7, panel (d)), both comparable to the performance of aptamers generated using modified bases (Gold et al. (2010) *PloS one* 5, e15004). The sequences of the above aptamers and their binding affinities are provided below in Table 6 (From top to bottom SEQ ID NOs:2, 9, 10 and 18).

TABLE 6

The sequences of the top-binding aptamers and their affinities.

| Clone ID | Selected region (5' to 3')[a] | $K_d$ |
|---|---|---|
| Thrombin 03 | CAGCGCTAGGGCTTTTAGCGTAATGGGTAGG GTGGTGCGGTGCAGATATCGGAATTGGTG | 7.04 pM |
| ApoE 06 | GATAAACGCCTTGATTAAAGGCCCAGTTCTT TAGGCCTACACGTGCTGCGACATTAATT | 938 pM |
| PAI-1 01 | CATTGAGATAGCTAGTTGTAGCTGCGTCATA GGCTGGGTTGGGTCTAGTGGTTGGGTGTG | 339 pM |
| 4-1BB 07 | GTCAGATTCCACTATAGTAGGTTGGGTAGGG TGGTCGCAGTGGATGATATGTCGTAGGGG | 2.32 nM |

[a]Only the variable sequence (60-mer) is shown in the table, but affinity measurements were performed with full-length (100-mer) molecules containing the flanking PCR primer-binding sites.

Example 5: Theoretical Basis of Particle Display

1. Methods and Materials

Particle display may exploit the fact that the fluorescence intensity of each AP is proportional to the affinity of the aptamer displayed on its surface towards the target. Quantitatively, the mean fluorescence intensity (F) of an AP displaying an aptamer with an equilibrium dissociation constant of $k_d$ can be expressed as $$F = \frac{[T]}{[T] + k_d} \times (F_{max} - F_{bg}) + F_{bg} \quad \text{Eq. 1}$$

where [T] is the concentration of the fluorescently labeled target, $F_{bg}$ is the mean background fluorescence of the APs, and $F_{max}$ is the maximum mean fluorescence when an AP is saturated with labeled target. Thus, if one takes a population of APs and ranks them ($AP^i$, i=1, 2, ..., n) according to the affinity of the aptamers displayed on their surfaces (i.e., $k_d^1 < k_d^2 < ... < k_d^n$), wherein $AP^1$ is the particle displaying the highest affinity aptamer, then $F^1 > F^2 > ... > F^n$. Because FACS employs logarithmic amplification electronics, the fluorescence signal is presented on a logarithmic scale. Therefore, on a FACS plot, the separation between $AP^1$ and any other $AP^i$ corresponds to the ratio of their mean fluorescence, $Fr^i$:

$$Fr^i = \frac{F^1}{F^i} = \frac{\left(\frac{[T]}{k_d^1}\right)^2 + \left(\frac{F_{bg}}{F_{max}} + \frac{k_d^i}{k_d^1}\right)\frac{[T]}{k_d^1} + \frac{F_{bg}}{F_{max}}\frac{k_d^i}{k_d^1}}{\left(\frac{[T]}{k_d^1}\right)^2 + \left(1 + \frac{F_{bg}}{F_{max}}\frac{k_d^i}{k_d^1}\right)\frac{[T]}{k_d^1} + \frac{F_{bg}}{F_{max}}\frac{k_d^i}{k_d^1}} \quad \text{Eq. 2}$$

$$(i = 1, 2, \ldots, n)$$

It was observed that $Fr^i$ is dependent on one experimentally measurable system constant, $F_{max}/F_{bg}$, and two dimensionless variables, $[T]/k_d^1$ and $k_d^i/k_d^1 = k_d r^i$. Thus, for a given $k_d r^i$, $[T]/k_d^1$ is the only variable that determines both $Fr^i$ and $F^1$. In the experimental system discussed in the examples above, $F_{max}$ and $F_{bg}$ were measured to be 7500 a.u. and 250 a.u., respectively. Using these values, $Fr^i$ was plotted as a function of $F^1/F_{max}$ for a range of $2 < k_d r^i < 10$ (FIG. 3, panel (a)). It was observed that as $F^1$ increases, $Fr^i$ increases until it reaches an optimal value, $(F^1)_{opt}^i$, after which it decreases monotonically to 1.

In order to identify the $(F^1)_{opt}^i$ that enables maximum separation between $AP^1$ and $AP^i$, the optimal $[T]/k_d^1$ that results in maximum $Fr^i$ was first analysed. To do so, the derivative of Eq. 2 with respect to [T] was taken and set to equal 0. The solution to this equation is $$\left(\frac{[T]}{k_d^1}\right)_{opt}^i = \sqrt{\frac{F_{bg}}{F_{max}} k_d r^i} \quad \text{Eq. 3}$$

$$(i = 1, 2, \ldots, n).$$

Next, $(F^1)_{opt}^i$ was calculated by substituting Eq. 3 into Eq. 1.

$$(F^1)_{opt}^i = \frac{1+\sqrt{\frac{F_{bg}}{F_{max}k_d r^i}}}{1+\sqrt{\frac{F_{max}}{F_{bg}k_d r^i}}} F_{max} \quad \text{Eq. 4}$$

$$(i = 1, 2, \ldots, n)$$

Figure 3:
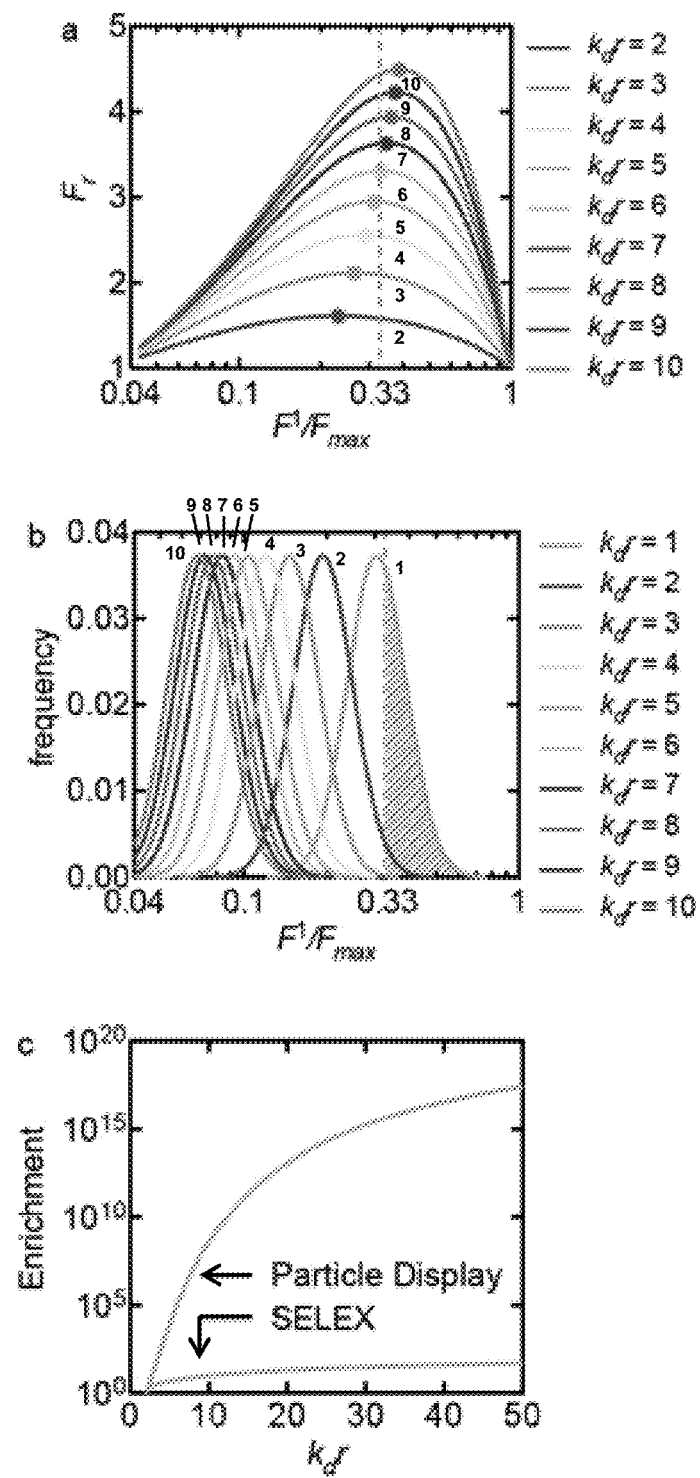
FIG. 3: Particle display performance parameters. (Panel (a)) The fluorescence intensity ratio (Fr) of $AP^1/AP^i$ ($k_d r^i$=2, 3, ..., 10) plotted as a function of $F^1/F_{max}$. The optimal value for ($F^1/F_{max}$) shifts from 0.23 to 0.38 as $k_d r$ increases. Setting $F^1 = F_{max}/3$ ensures that $Fr^i$ is within 2% of the optimal value for APs where $2 < k_d r < 10$, enabling maximum separation between $AP^1$ and $AP^i$. (Panel (b)) Fluorescence distribution of $AP^1$ and $AP^i$ (log-normal probability density function with CV of 25%). When $F^1 = F_{max}/3$, the shaded region represents the fraction of $AP^i$ whose fluorescence exceeds the threshold and is collected by FACS. (Panel (c)) Enrichment of $AP^1$ over $AP^i$ as a function of $k_d r$. Particle display performance significantly exceeds the theoretical limit of selection-based methods.

Using Eq. 4, the analytical solution of $(F^1)_{opt}^i$ was calculated for a range of $2<k_d r<10$ to be $0.23<(F^1)_{opt}^i/F_{max}<0.38$ (denoted by * in FIG. 3, panel (a)). This narrow range near $k_d^1$ was chosen because effective isolation of $AP^1$ in this range would ensure exclusion of APs with larger $k_d r$. It is noted that setting $F^1 \approx F_{max}/3$ is a useful experimental guideline for the particle display method, ensuring that $Fr^i$ is within 2% of the optimal value for APs in the range of $2<k_d r<10$, enabling maximum separation between $AP^1$ and $AP^i$.

Next, the enrichment performance after one round of particle display screening using $F^1 = F_{max}/3$ was calculated. To do so, the fluorescence distribution of the APs was first measured and it was verified that the distribution was indeed log-normal as previously reported. Thus, the fluorescence distribution of each $AP^i$ can be defined by the mean fluorescence ($F^i$) and the coefficient of variance ($CV^i$), which represents the variability of the fluorescence distribution. The [T] that results in $F^1 = F_{max}/3$ was determined, and this [T] was substituted into Eq. 1 to calculate $F^i$. The $CV^i$ was experimentally determined to be 25% from FACS measurements. From these values, the fluorescence distribution of the APs was obtained (FIG. 3, panel (b)). Next, the sort gate was set at $F_{max}/3$, and the fraction of $AP^i$ whose fluorescence exceeds that threshold (FIG. 3, panel (b), shaded) and would therefore be collected by FACS was calculated.

2. Results

Figure 2:
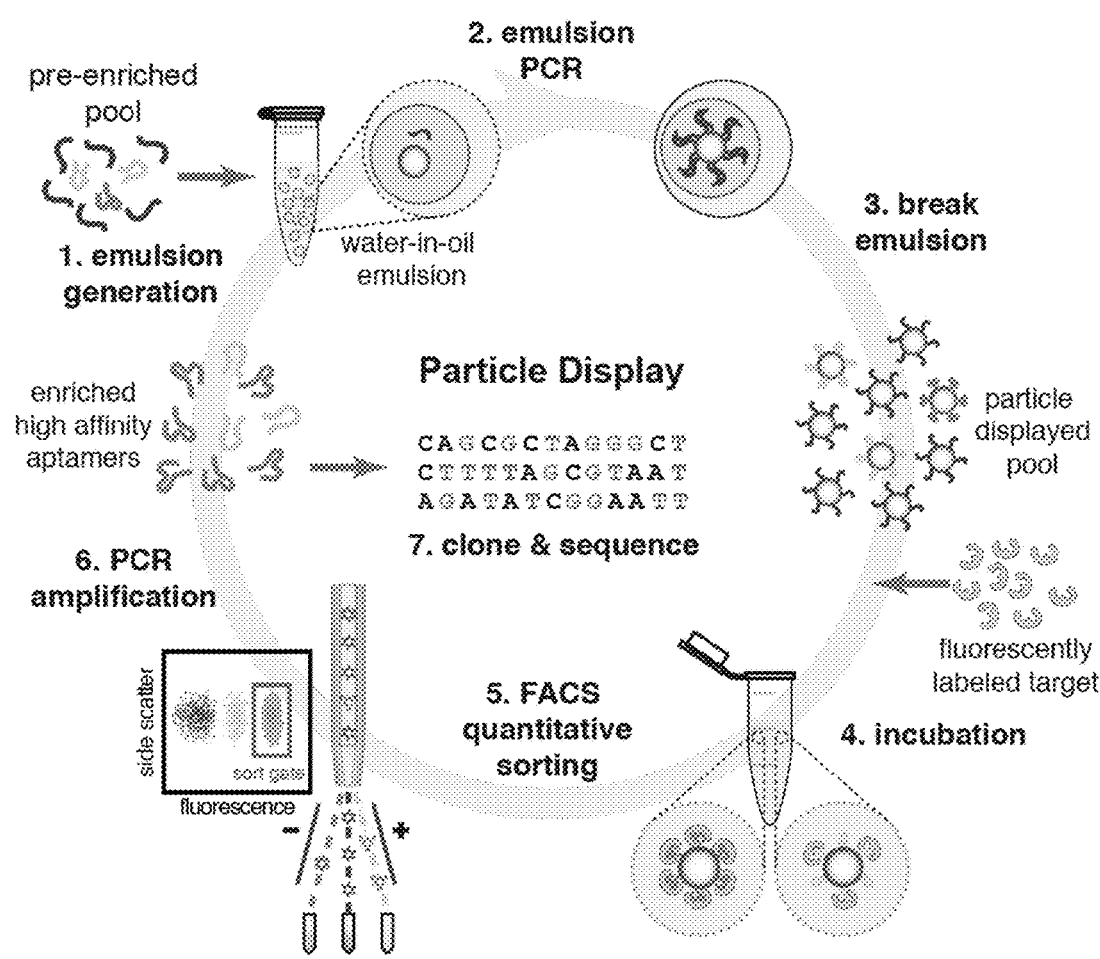
FIG. 2: Particle display system overview.

The enrichment of $AP^1$ over $AP^i$ was obtained by taking the ratio of the collected $AP^1$ and $AP^i$ (FIG. 2, panel (c), top curve), and it was determined that the enrichment performance of particle display significantly exceeds the theoretical limit of any selection-based method, which is well known to be $k_d r$ (see, e.g., Wang et al. *PLoS ONE* 7, e43940 (2012), and Vant-Hull et al. *Current protocols in nucleic acid chemistry/edited* by Serge L. Beaucage . . . [et al.] Chapter 9, Unit 9.1 (2000)) (FIG. 2, panel (c), bottom curve). For example, for $k_d r = 50$, one can achieve an enrichment of $3 \times 10^{17}$ in a single round of particle display, while it is not theoretically possible to exceed enrichment of 50 using selection-based methods. Particle display therefore exhibits an unprecedented capacity to discriminate between APs that display aptamers with similar affinities with high resolution. For example, particle display can achieve 445-fold enrichment of a high-affinity aptamer relative to other aptamers with just three-fold lower affinity, whereas only three-fold relative enrichment of such aptamers is possible through selection-based methods.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for screening a mixture of candidate aptamer sequences, the method comprising:
   exposing a plurality of aptamer particles to a target, wherein each of the aptamer particles is immobilized with only a subset of the candidate aptamer sequences, and wherein the subset is present in multiple copies;
   quantitating a signal for each of the aptamer particles, wherein the signal, when present, is indicative of a desired property between the candidate aptamer sequence bound to each aptamer particle and the target; and
   sorting each of the aptamer particles based on the quantitated signal for each aptamer particle.

2. The screening method of claim 1, wherein the target is a protein target or a small molecule target.

3. The screening method of claim 1, wherein the candidate aptamer sequences are DNA sequences.

4. The screening method of claim 1, wherein one or more of the candidate aptamer sequences comprises a molecule conjugated thereto, wherein the molecule conjugated thereto is a small molecule, a fluorophore, a peptide, or an siRNA.

5. The screening method of claim 1, wherein the desired property is a target binding activity or a target-binding induced activity.

6. The screening method of claim 5, wherein the target binding activity is affinity, specificity or bi-specificity.

7. The screening method of claim 6, wherein the target binding activity is specificity, the screening method comprises exposing the plurality of particles to a first target and a second target, and wherein the candidate aptamer sequences having the desired property exhibit a specific binding affinity for either the first target or the second target but not both.

8. The screening method of claim 6, wherein the target binding activity is bi-specificity, the screening method comprises exposing the plurality of particles to a first target and a second target, and wherein the candidate aptamer sequences having the desired property exhibit a specific binding affinity for both the first and second target.

9. The screening method of claim 1, wherein the plurality of particles comprises from $1 \times 10^2$ to $1 \times 10^{14}$ particles.

10. The screening method of claim 1, wherein the sequence diversity of the mixture is from $1 \times 10^2$ to $1 \times 10^{14}$.

11. The screening method of claim 1, wherein each of the particles of the plurality of particles comprises from $1 \times 10^2$ to $1 \times 10^{10}$ candidate aptamer sequences bound thereto.

12. The screening method of claim 1, wherein the sequence diversity of the subset of the candidate aptamer sequences immobilized on any one of the plurality of particles is from 1 to 106.

13. The screening method of claim 12, wherein the sequence diversity of the subset of the candidate aptamer sequences immobilized on any one of the plurality of particles is 1.

14. The screening method of claim 1, wherein the particle or particles that comprise one or more candidate aptamer sequences having the desired property are modified as a result of the desired property following exposure to the target, which modification allows the particle or particles that comprise the more candidate aptamer sequences having the desired property to be isolated, wherein the modification results in a physically detectable change, a chemically detectable change, or an optically detectable change.

15. The screening method of claim 1, wherein the sorting step comprises sorting the plurality of particles using fluorescence activated cell sorting (FACS).

16. The method of claim 1, further comprising isolating a particle or particles from the plurality of particles, wherein the isolated particle or particles comprise one or more candidate aptamer sequences having the desired property.

17. The method of claim 16, further comprising identifying one or more aptamer sequences having the desired property from the isolated particle or particles.

18. The screening method of claim 17 further comprising introducing one or more mutations into the more aptamer sequences having the desired property.

19. The screening method of claim 17, further comprising a step of amplifying the sequences of the one or more aptamer sequences identified as having the desired property, and iteratively repeating one or more of the exposing, isolating, identifying, and amplifying steps.

* * * * *